United States Patent
Harty et al.

(10) Patent No.: US 10,517,276 B2
(45) Date of Patent: Dec. 31, 2019

(54) METHOD, A DEVICE AND A SYSTEM FOR DETECTING A STATE OF AN ANIMAL

(71) Applicant: DAIRYMASTER, Causeway (IE)

(72) Inventors: Edmond Patrick Harty, Ballyheigue (IE); Liam Eoghan Mullane, Newcastlewest (IE); John Gerard Daly, Tralee (IE)

(73) Assignee: DAIRYMASTER, County Kerry (IE)

( * ) Notice: Subject to any disclaimer, the term of this patent is extended or adjusted under 35 U.S.C. 154(b) by 421 days.

(21) Appl. No.: 14/897,496

(22) PCT Filed: Jun. 16, 2014

(86) PCT No.: PCT/IE2014/000009
§ 371 (c)(1),
(2) Date: Dec. 10, 2015

(87) PCT Pub. No.: WO2014/199361
PCT Pub. Date: Dec. 18, 2014

(65) Prior Publication Data
US 2016/0165851 A1    Jun. 16, 2016

(30) Foreign Application Priority Data

Jun. 14, 2013 (IE) .................................. S2013/0193
Jun. 14, 2013 (IE) .................................. S2013/0194

(51) Int. Cl.
*A01K 29/00* (2006.01)
*A01K 11/00* (2006.01)
(Continued)

(52) U.S. Cl.
CPC .......... *A01K 29/005* (2013.01); *A01K 11/006* (2013.01); *A61B 5/0022* (2013.01);
(Continued)

(58) Field of Classification Search
CPC .. A01K 29/005; A01K 11/006; A61B 5/0022; A61B 5/1114; A61B 5/1118;
(Continued)

(56) References Cited

U.S. PATENT DOCUMENTS

| | | | |
|---|---|---|---|
| 2004/0097814 A1* | 5/2004 | Navakatikyan | A61B 5/024 600/485 |
| 2007/0130893 A1* | 6/2007 | Davies | A01K 11/008 54/1 |

(Continued)

FOREIGN PATENT DOCUMENTS

| JP | 2003-219757 A | 8/2003 |
|---|---|---|
| WO | 97/24027 A1 | 7/1997 |
| WO | 2011/069512 A1 | 6/2011 |

OTHER PUBLICATIONS

International Search Report of PCT/IE2014/000009 dated Sep. 3, 2014.
European Search Report dated Sep. 27, 2018 in EP 14 736 032.5.

*Primary Examiner* — Daniel L Cerioni
(74) *Attorney, Agent, or Firm* — Sughrue Mion, PLLC

(57) ABSTRACT

A device (5) attached to the neck (6) of an animal (2) comprises an accelerometer (28) which produces first and second signals indicative of movement of the animal (2) and the raised and lowered states of the head of the animal. A microprocessor (30) in the device (5) processes the first and second signals to detect ruminating, resting, feeding and three activity states of the animal during respective second predefined time periods of approximately 15 minutes duration. Data indicative of the states of the animal is stored by the microprocessor (30) in the device (5) and periodically transmitted to a cloud computer server which further processes the data to determine various health states and other issues of the animal.

27 Claims, 9 Drawing Sheets

Figure 1:
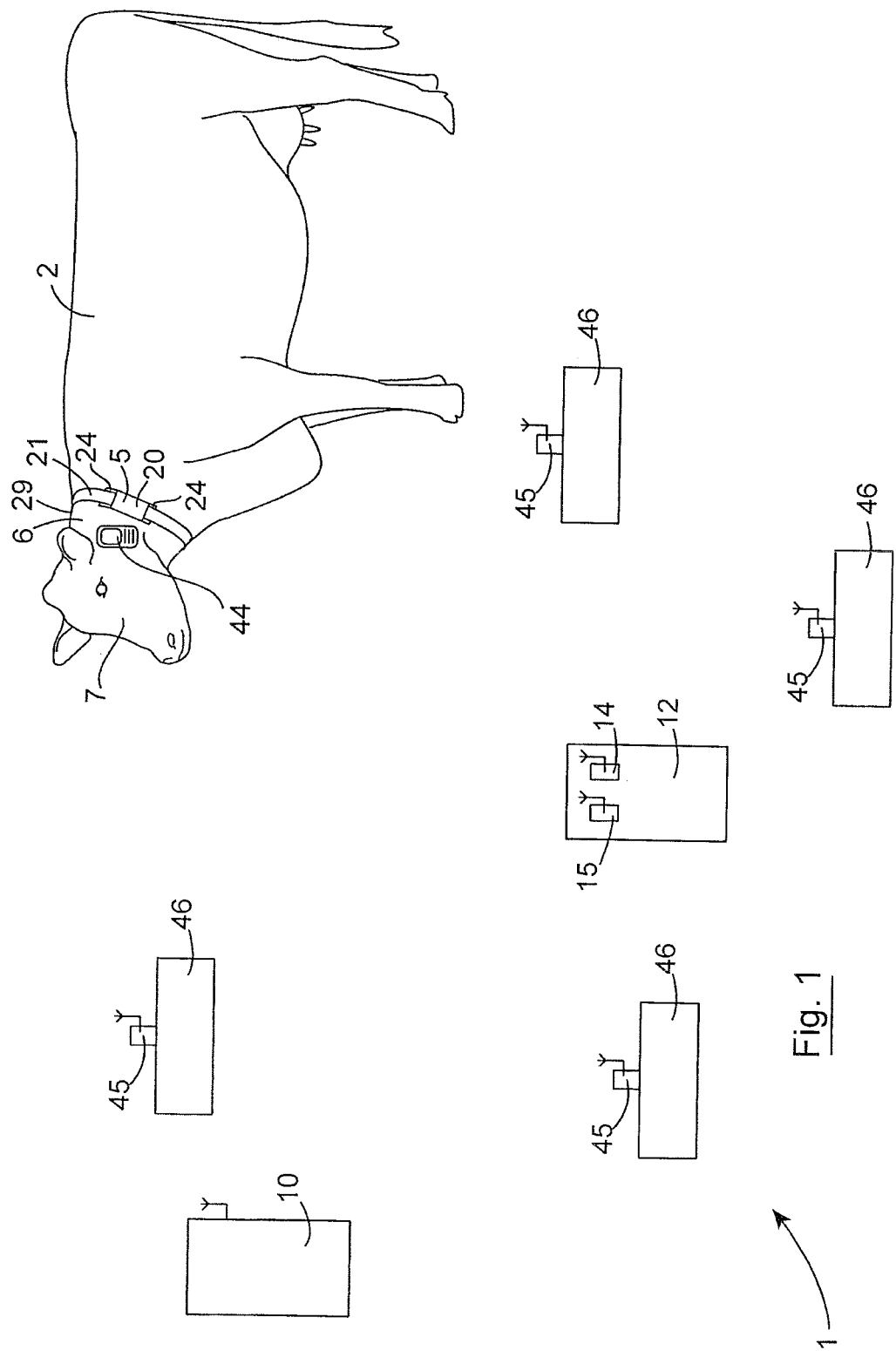

(51) Int. Cl.
*A61B 5/00* (2006.01)
*A61B 5/11* (2006.01)
(52) U.S. Cl.
CPC .......... *A61B 5/1114* (2013.01); *A61B 5/1118* (2013.01); *A61B 5/1121* (2013.01); *A61B 5/1123* (2013.01); *A61B 5/7246* (2013.01); *A61B 5/7278* (2013.01); *A61B 5/7282* (2013.01); *A61B 2503/40* (2013.01); *A61B 2562/0219* (2013.01)
(58) Field of Classification Search
CPC ... A61B 5/1121; A61B 5/1123; A61B 5/7246; A61B 5/7278; A61B 5/7282
USPC ......................................................... 600/595
See application file for complete search history.

(56) References Cited

U.S. PATENT DOCUMENTS

| | | | | |
|---|---|---|---|---|
| 2008/0021352 | A1* | 1/2008 | Keegan | A61B 5/0002 600/595 |
| 2009/0037056 | A1* | 2/2009 | Erb | B60R 21/0132 701/46 |
| 2012/0186091 | A1* | 7/2012 | Yao | G01C 17/30 33/355 R |
| 2012/0274442 | A1* | 11/2012 | Mottram | A01K 29/005 340/5.8 |
| 2014/0275824 | A1* | 9/2014 | Couse | A01K 29/005 600/301 |
| 2014/0347262 | A1* | 11/2014 | Paek | G09G 3/20 345/156 |
| 2015/0351885 | A1* | 12/2015 | Kool | A61D 17/002 600/551 |

* cited by examiner

METHOD, A DEVICE AND A SYSTEM FOR DETECTING A STATE OF AN ANIMAL

CROSS REFERENCE TO RELATED APPLICATIONS

This application is a National Stage of International Application No. PCT/IE2014/000009 filed Jun. 16, 2014 claiming priority based on Irish Patent Application Nos. S2013/0193 filed Jun. 14, 2013 and S2013/0194 filed Jun. 14, 2013, the contents of each of which are incorporated herein by reference in their entirety.

The present invention relates to a method for detecting the state of an animal, and the invention also relates to a device for detecting the state of the animal. Further, the invention relates to a system for detecting the state of an animal.

Devices and methods for detecting the state of an animal are known. Such devices, typically, are electronic devices and they may include sensors, for monitoring, for example, the temperature, heart rate, blood pressure and the like of an animal. Other such devices are provided for detecting when an animal is in a state of relatively high activity in order to facilitate in the detection of oestrus in the animal. Attempts have been made to provide methods and devices for detecting other states of an animal, for example, for detecting when an animal is feeding or ruminating. However, to date such methods and devices lack accuracy.

There is therefore a need for a method for detecting at least one state of an animal, for example, ruminating, resting, feeding or the like, which addresses lack of accuracy issues of known methods and devices. There is also a need for a device and a system for detecting at least one of such states of an animal which addresses accuracy issues of known methods and devices.

The present invention is directed towards providing such a method, a device and a system.

According to the invention there is provided a method for detecting at least one detectable state of an animal, the method comprising:
  computing a mean magnitude value of a first signal indicative of movement of the head of the animal from an acceleration sensor attached to the animal during each first predefined time period of a plurality of first predefined time periods,
  counting the numbers of positive and negative peaks of the first signal during each first predefined time period, the absolute magnitude values of which with reference to the mean magnitude value lie within a predefined range of absolute magnitude values,
  computing the maximum peak to peak value of the first signal during each first predefined time period as the sum of the absolute magnitude values of the maximum positive peak value with reference to the mean magnitude value and the maximum negative peak value with reference to the mean magnitude value of the first signal during the corresponding first predefined time period, and
  detecting the at least one detectable state of the animal during each first predefined time period in response to at least one of
  the value of the count of the positive and negative peak values of the first signal which lie within the predefined range of absolute magnitude values during the corresponding first predefined time period, and
  the computed maximum peak to peak value of the first signal during the corresponding first predefined time period.

In one aspect of the invention lower and upper absolute magnitude values of the predefined range of absolute magnitude values of the first signal for each first predefined time period are defined as respective functions of the mean magnitude value of the first signal during the corresponding first predefined time period.

Preferably, the lower absolute magnitude value of the predefined range of absolute magnitude values of the first signal for each first predefined time period lies within a first predefined range of percentage values of the mean magnitude value of the first signal during the corresponding first predefined time period.

In one embodiment of the invention the first predefined range of percentage values within which the lower absolute magnitude value of the predefined range of absolute magnitude values of the first signal for each first predefined time period is 0.1% to 1% of the mean magnitude value of the first signal during the corresponding first predefined time period. Preferably, the first predefined range of percentage values within which the lower absolute magnitude value of the predefined range of absolute magnitude values of the first signal for each first predefined time period is 0.3% to 0.7% of the mean magnitude value of the first signal during the corresponding first predefined time period. Advantageously, the lower absolute magnitude value of the predefined range of absolute magnitude values of the first signal for each first predefined time period is approximately 0.5% of the mean magnitude value of the first signal during the corresponding first predefined time period.

In another aspect of the invention the upper absolute magnitude value of the predefined range of absolute magnitude values of the first signal for each first predefined time period lies within a second predefined range of percentage values of the mean magnitude value of the first signal during the corresponding first predefined time period.

In another embodiment of the invention the second predefined range of percentage values within which the upper absolute magnitude value of the predefined range of absolute magnitude values of the first signal for each first predefined time period is 7% to 13% of the mean magnitude value of the first signal during the corresponding first predefined time period. Preferably, the second predefined range of percentage values within which the upper absolute magnitude value of the predefined range of absolute magnitude values of the first signal for each first predefined time period is 8% to 12% of the mean magnitude value of the first signal during the corresponding first predefined time period. Advantageously, the upper absolute magnitude value of the predefined range of absolute magnitude values of the first signal for each first predefined time period is approximately 10% of the mean magnitude value of the first signal during the corresponding first predefined time period.

In one embodiment of the invention one of the detectable states of the animal is ruminating, and ruminating is detected in any one of the first predefined time periods in response to at least one of:
  the count of the positive and negative peaks of the first signal which lie within the predefined range of absolute magnitude values exceeding a predefined ruminating threshold count during the corresponding first predefined time period, and
  the computed maximum peak to peak value of the first signal lying between a lower predefined peak to peak threshold value and an upper predefined peak to peak threshold value during the corresponding first predefined time period.

In another embodiment of the invention ruminating is detected in any one of the first predefined time periods in response to the count of the positive and negative peaks of the first signal which lie within the predefined range of absolute magnitude values exceeding a predefined ruminating threshold count during the corresponding first predefined time period, and the computed maximum peak to peak value of the first signal lying between the lower predefined peak to peak threshold value and the upper predefined peak to peak threshold value during the corresponding first predefined time period.

In one aspect of the invention the predefined ruminating threshold count is a function of the duration of the first predefined time period.

In another aspect of the invention the lower predefined peak to peak threshold value of the first signal for each first predefined time period is defined as a function of the computed mean magnitude value of the first signal during the corresponding first predefined time period. Preferably, the lower predefined peak to peak threshold value of the first signal for each first predefined time period is defined as a percentage value of the computed mean magnitude value of the first signal during the corresponding first predefined time period.

In one embodiment of the invention the lower predefined peak to peak threshold value of the first signal for each first predefined time period lies in the range of 1% and 7% of the computed mean magnitude value of the first signal during the corresponding first predefined time period. Preferably, the lower predefined peak to peak threshold value of the first signal for each first predefined time period lies in the range of 2% and 6% of the computed mean magnitude value of the first signal during the corresponding first predefined time period. Advantageously, the lower predefined peak to peak threshold value of the first signal for each first predefined time period is approximately 4% of the computed mean magnitude value of the first signal during the corresponding first predefined time period.

In another aspect of the invention the upper predefined peak to peak threshold value of the first signal for each first predefined time period is defined as a function of the computed mean magnitude value of the first signal during the corresponding first predefined time period. Preferably, the upper predefined peak to peak threshold value of the first signal for each first predefined time period is defined as a percentage value of the computed mean magnitude value of the first signal during the corresponding first predefined time period.

In another embodiment of the invention the upper predefined peak to peak threshold value of the first signal for each first predefined time period lies in the range of 16% to 22% of the computed mean magnitude value of the first signal during the corresponding first predefined time period. Preferably, the upper predefined peak to peak threshold value for each first predefined time period lies in the range of 18% to 21% of the computed mean magnitude value of the first signal during the corresponding first predefined time period. Advantageously, the upper predefined peak to peak threshold value for each first predefined time period is approximately 19.5% of the computed mean magnitude value of the first signal during the corresponding first predefined time period.

In another embodiment of the invention one of the detectable states of the animal is resting, and resting is detected in any one of the first predefined time periods in response to at least one of the count of the positive and negative peaks of the first signal which lie within the predefined range of absolute magnitude values not exceeding the ruminating predefined threshold count during the corresponding first predefined time period, and the computed maximum peak to peak value of the first signal not exceeding a resting predefined peak to peak threshold value during the corresponding first predefined time period.

In a further embodiment of the invention one of the detectable states of the animal is resting, and resting is detected in any one of the first predefined time periods in response to the count of the positive and negative peaks of the first signal which lie within the predefined range of absolute magnitude values not exceeding the ruminating predefined threshold count during the corresponding first predefined time period, and the computed maximum peak to peak value of the first signal not exceeding the resting predefined peak to peak threshold value during the corresponding first predefined time period.

In one aspect of the invention the resting predefined peak to peak threshold value of the first signal for each first predefined time period is defined as a function of the computed mean magnitude value of the first signal during the corresponding first predefined time period. Preferably, the resting predefined peak to peak threshold value of the first signal for each first predefined time period is defined as a percentage of the computed mean magnitude value of the first signal during the corresponding first predefined time period.

In one embodiment of the invention the resting predefined peak to peak threshold value of the first signal for each first predefined time period is not greater than 30% of the computed mean magnitude value of the first signal during the corresponding first predefined time period. Preferably, the resting predefined peak to peak threshold value of the first signal for each first predefined time period is not greater than 23% of the computed mean magnitude value of the first signal during the corresponding first predefined time period. Advantageously, the resting predefined peak to peak threshold value of the first signal for each first predefined time period is approximately 20% of the computed mean magnitude value of the first signal during the corresponding first predefined time period.

In one embodiment of the invention one of the detectable states of the animal is a feeding state, and feeding is detected in any one of the first predefined time periods in response to at least one of the maximum peak to peak value of the first signal being greater than or equal to the resting predefined peak to peak threshold value during the corresponding first predefined time period, and either one of the following:

the count of the positive and negative peaks of the first signal, the absolute magnitude values of which lie within the predefined range of absolute magnitude values exceeding a predefined feeding threshold count during the corresponding first predefined time period, and a second signal from a head status sensor attached to the animal indicative of raised and lowered states of the head of the animal being indicative of the head of the animal being in the lowered state during the corresponding first predefined time period.

In one aspect of the invention the acceleration sensor comprises the head status sensor, and the acceleration sensor produces the second signal indicative of the raised and lowered states of the head of the animal.

In another aspect of the invention the mean magnitude value of the second signal is computed during each first predefined time period, and the raised and lowered states of the head of the animal is detected in response to the computed mean magnitude value of the second signal during the corresponding first predefined time period.

In one embodiment of the invention the head of the animal is detected as being in the lowered state in response to the computed mean magnitude value of the second signal being one of greater than and lower than a predefined mean magnitude value.

In another aspect of the invention the predefined mean magnitude value of the second signal for each first predefined time period is defined as a function of the respective magnitude values of the second signal corresponding to the head of the animal being in the lowest of the lower states and the highest of the raised states.

Preferably, the predefined mean magnitude value of the second signal for each first predefined time period is a value indicative of the head of the animal being at a level sufficient for grazing or feeding from a trough at ground level.

In one aspect of the invention the predefined feeding threshold count is a function of the duration of the first predefined time period.

In a further embodiment of the invention one of the detectable states of the animal is an active state, and the active state is detected at the end of any one of the first predefined time periods in response to the animal being detected as not being ruminating, resting or feeding.

In a still further embodiment of the invention one of the detectable states of the animal is a high activity state, and the high activity state is detected during any one of the first predefined time periods in response to the count of the positive and negative peaks of the first signal, the absolute magnitude values of which with reference to the mean magnitude value of the first signal exceed a first predefined peak threshold value during the corresponding first predefined time period exceeding a first predefined peak threshold count during that corresponding first predefined time period.

In one aspect of the invention the first predefined peak threshold value of the first signal for each first predefined time period is defined as a function of the computed mean magnitude value of the first signal during the corresponding first predefined time period. Preferably, the first predefined peak threshold value of the first signal for each first predefined time period is defined as a percentage value of the computed mean magnitude value the first signal during the corresponding first predefined time period.

In one embodiment of the invention the first predefined peak threshold value of the first signal for each first predefined time period is not less than 30% of the computed mean magnitude value of the first signal during the corresponding first predefined time period. Preferably, the first predefined peak threshold value of the first signal for each first predefined time period is not less than 33% of the computed mean magnitude value of the first signal during the corresponding first predefined time period. Advantageously, the first predefined peak threshold value of the first signal for each first predefined time period is approximately 35% of the computed mean threshold value of the first signal during the corresponding first predefined time period.

In another embodiment of the invention the first predefined peak threshold count is a function of the duration of the first predefined time period.

In one embodiment of the invention one of the detectable states of the animal is a medium activity state, and the medium activity state is detected in any one of the first predefined time periods in response to one of the count of the positive and negative peaks of the first signal, the absolute magnitude values of which with reference to the mean magnitude value of the first signal exceed the first predefined peak threshold value lying between a second predefined peak threshold count and one less than the first predefined peak threshold count during the corresponding first predefined time period, and the count of the positive and negative peaks of the first signal, the absolute magnitude values of which with reference to the mean magnitude value of the first signal exceed a second predefined peak threshold value during the corresponding first predefined time period exceeding a third predefined peak threshold count during that corresponding first time period.

In one aspect of the invention the second predefined peak threshold count is a function of the duration of the first predefined time period.

In another aspect of the invention the third predefined peak threshold count is a function of the duration of the first predefined time period.

In a further aspect of the invention the second predefined peak threshold value of the first signal for each first predefined time period is defined as a function of the computed mean magnitude value of the first signal during the corresponding first predefined time period. Preferably, the second predefined peak threshold value of the first signal for each first predefined time period is defined as a percentage value of the computed mean magnitude value of the first signal during the corresponding first predefined time period.

In one embodiment of the invention the second predefined peak threshold value of the first signal for each first predefined time period is greater than 5% of the computed mean magnitude value of the first signal during the corresponding first predefined time period. Preferably, the second predefined peak threshold value of the first signal for each first predefined time period is greater than 8% of the computed mean magnitude value of the first signal during the corresponding first predefined time period. Advantageously, the second predefined peak threshold value of the first signal for each first predefined time period is approximately 10% of the computed mean magnitude value of the first signal during the corresponding first predefined time period.

In another embodiment of the invention one of the detectable states of the animal is a low activity state, and the low activity state is detected in response to the computed maximum peak to peak value of the first signal exceeding the resting predefined peak to peak threshold value during the corresponding first predefined time period, and the count of the positive and negative peaks, the absolute magnitude values of which with reference to the mean magnitude value of the first signal exceed the second predefined peak threshold value during the corresponding first predefined time period being less than the third predefined peak threshold count during that corresponding first time period.

In another embodiment of the invention the first signal is sampled to obtain a plurality of sampled values indicative of the magnitude of the first signal at respective sampling points during each first predefined time period.

In another embodiment of the invention the mean magnitude value of the first signal is computed for each first predefined time period from the sampled magnitude values of the first signal during the corresponding first predefined time period.

In a further embodiment of the invention the absolute values of the positive and negative peaks of the first signal with reference to the mean magnitude value of the first signal are computed for each first predefined time period from the sampled magnitude values of the first signal during the corresponding first predefined time period.

In a still further embodiment of the invention the maximum peak to peak value of the first signal is computed for each first predefined time period from the sampled magnitude values of the first signal during the corresponding first predefined time period.

Preferably, the second signal is sampled to obtain a plurality of sampled values indicative of the magnitude of the second signal at respective sampling points during each first predefined time period.

Advantageously, the mean magnitude value of the second signal is computed for each first predefined time period from the sampled magnitude values of the second signal during the corresponding first predefined time period.

In one embodiment of the invention the acceleration sensor comprises an accelerometer configured to produce the first signal indicative of acceleration to which the accelerometer is subjected along a first axis thereof, and the second signal indicative of acceleration to which the accelerometer is subjected along a second axis thereof perpendicular to the first axis.

Preferably, the accelerometer is attached to the animal with the first axis thereof extending substantially perpendicularly to the back of the neck of the animal, and in a generally upwardly, downwardly direction. Advantageously, the accelerometer is attached to the animal with the second axis thereof extending substantially parallel to the back of the neck of the animal. Ideally, the accelerometer is attached to the neck of the animal.

In one embodiment of the invention the accelerometer is attached to the animal by a securing ligature extending around the neck of the animal.

In one embodiment of the invention the acceleration sensor is located in a housing.

Preferably, a signal processor is provided in the housing for processing the first and second signals and for determining the state of the animal during the respective first predefined time periods.

In one embodiment of the invention the numbers of the first predefined time periods the animal is detected as being in the respective states is stored and cross-referenced with the identity of the corresponding states. Preferably, the numbers of the first predefined time periods the animal is detected as being in the respective states is stored and cross-referenced with the identity of the corresponding states at the end of each of a plurality of second predefined time periods. Advantageously, the numbers of the first predefined time periods the animal is detected as being in the respective states is stored and cross-referenced with the identity of the corresponding states and is analysed. Ideally, the numbers of the first predefined time periods the animal is detected as being in the respective states is stored and cross-referenced with the identity of the corresponding states and is analysed by a computing means.

In one embodiment of the invention the computing means is a remotely located computing means. Preferably, the stored data relating to the numbers of first predefined time periods the animal is in the respective states cross-referenced with the respective states during the second predefined time periods is wirelessly communicated to the remotely located computing means. Advantageously, the stored data relating to the numbers of first predefined time periods the animal is in the respective states cross-referenced with the respective states during the second predefined time periods is wirelessly communicated to the remotely located computing means by a relay station.

In one aspect of the invention the computing means comprises one of a cloud computer server and a computer.

In one embodiment of the invention the health condition of an animal is determined from the stored data comprising the respective states of the animal cross-referenced with the numbers of first predefined time periods the animal is in the respective states during the corresponding second predefined time periods.

In another embodiment of the invention the first predefined time period lies in the range of 5 seconds to 25 seconds. Preferably, the first predefined time period is approximately 11.5 seconds.

In another embodiment of the invention the second predefined time period is of duration up to 60 minutes. Preferably, the second predefined time period is of duration of approximately 15 minutes.

In a further embodiment of the invention the sampling rate at which the first and second signals are sampled lies in the range of 6 Hz to 50 Hz. Preferably, the sampling rate at which the first and second signals are sampled is approximately 11 Hz.

Preferably, the first predefined time periods run consecutively one after the other. Advantageously, the second predefined time periods run consecutively one after the other.

In one embodiment of the invention data indicative of at least one predefined location visited by the animal is stored. Preferably, the time at which the animal visited the at least one predefined location is stored. Advantageously, the duration of the visit to the at least one predefined location is stored.

In one aspect of the invention the identity of the at least one predefined location is determined from an identification signal received when the animal is adjacent the at least one predefined location. Preferably, the identification signal is received wirelessly. Advantageously, the identification signal is generated adjacent the at least one predefined location.

In one embodiment of the invention the identification signal is derived from a means adjacent the at least one predefined location capable of producing or configuring a signal to be indicative of the at least one predefined location. Preferably, the means for producing or configuring the signal to be indicative of the at least one predefined location comprises a means for wirelessly transmitting a signal indicative of the at least one predefined location.

In one aspect of the invention data indicative of a plurality of respective predefined locations visited by the animal is stored. Preferably, data indicative of a plurality of the respective times and the respective durations of the visits to the respective ones of the predefined locations are stored.

In another aspect of the invention the data indicative of the predefined locations, and preferably the times at which the predefined locations are visited, and advantageously, the durations of the visits to the predefined locations are transmitted to one of the base station and the cloud computer server.

In a further aspect of the invention the data indicative of the locations visited by the animal, the times at which the predefined locations are visited and the durations of the visits to the respective predefined locations are stored for each second predefined time period, and advantageously, are transmitted along with the data stored relating to the states of the animal for each of the second predefined time periods.

Additionally the invention provides a device for detecting at least one detectable state of an animal, the device being configured for locating on or in an animal and comprising an acceleration sensor, and a signal processor for carrying out the method according to the invention.

The invention also provides a device for detecting at least one detectable state of an animal, the device being configured for locating on or in the animal and comprising an acceleration sensor, and a signal processor, the signal processor being configured to
- compute a mean magnitude value of a first signal indicative of movement of the head of the animal from the acceleration sensor attached to the animal during each first predefined time period of a plurality of first predefined time periods,
- count the numbers of positive and negative peaks of the first signal during each first predefined time period, the absolute magnitude values of which with reference to the mean magnitude value lie within a predefined range of absolute magnitude values,
- compute the maximum peak to peak value of the first signal during each first predefined time period as the sum of the absolute magnitude values of the maximum positive peak value with reference to the mean magnitude value and the maximum negative peak value with reference to the mean magnitude value of the first signal during the corresponding first predefined time period, and
- detect the at least one detectable state of the animal during each first predefined time period in response to at least one of
  - the value of the count of the positive and negative peak values of the first signal which lie within the predefined range of absolute magnitude values during the corresponding first predefined time period, and
  - the computed maximum peak to peak value of the first signal during the corresponding first predefined time period.

In one embodiment of the invention the device comprises a housing, and preferably, the acceleration sensor is located in the housing.

In one aspect of the invention the signal processor is located in the housing.

Preferably, the signal processor is configured to store and cross-reference the numbers of the first predefined time periods the animal is detected as being in the respective states with the identity of the corresponding states.

In one embodiment of the invention the signal processor is configured to store data indicative of at least one predefined location visited by the animal.

Preferably, the time at which the animal visited the at least one predefined location is stored. Advantageously, the duration of the visit to the at least one predefined location is stored.

Preferably, the identity of the at least one predefined location is determined from an identification signal received when the animal is adjacent the at least one predefined location.

In another embodiment of the invention the device comprises a memory chip for storing an identifying code for identifying the device.

In a further embodiment of the invention the device comprises a wireless transceiver for transmitting data stored in the device relating to the numbers of the first predefined time periods that the animal is in the respective states cross-referenced with the corresponding states for reception by a remote computing means. Preferably, the wireless transmitter is selectively operable in a high power mode and a low power mode.

In another embodiment of the invention the device comprises an NFC module for facilitating communicating in an NFC protocol between the device and a powered mobile smart device.

In a further embodiment of the invention the device comprises a receiver for receiving an identification signal indicative of a predefined location visited by the animal.

Further the invention provides a system for determining at least one detectable state of an animal, the system comprising the device according to the invention, and a remote computing means configured to wirelessly receive data from the device indicative of the state of the animal.

Preferably, the remote computing means comprises one of a cloud computer server and a computer.

Advantageously, a relay station is provided for relaying data wirelessly received wirelessly from the device to the remote computing means.

Preferably, the relay station comprises a wireless transmitter for communicating with the device.

Advantageously, the relay station comprises a GSM module for communicating with the computing means.

Advantageously, the computing means is configured to determine the health condition of the animal from the data received from the device.

Preferably, the computing means is configured to determine issues relating to the animal from the data received from the device.

The advantages of the invention are many. One of the advantages, and in particular, one of the most important advantages of the invention is that it provides a device, a method and a system for detecting at least one state of an animal which detects the state with a relatively high degree of accuracy. Another advantage of the invention is that the device according to the invention is a relatively low power device, and accordingly, operates with a relatively long battery life. Indeed, it is envisaged that under normal use the device according to the invention could have a battery life of up to ten years. The fact that in general, transmission of data from the device only occurs when the device is in relatively close proximity to the relay station, the power required to drive the transceiver for communicating data with the relay station is relatively low. Furthermore, by virtue of the minimal processing of the sampled values of the first and second signals, the power requirement for processing the first and second signals by the microprocessor on board the device is also relatively low. Further energy saving by the device is achieved by virtue of the sequence with which the various states of the animal are detected.

The provision of the Near Field Communications module allows for uploading and downloading data to and from the device by a smart phone or other powered smart device with minimal usage of energy.

The provision of the wireless transceiver in the device to be operable in both a high power mode and a low power mode further facilitates in minimising the energy requirement of the device. The provision of the receiver for receiving identity data of respective predefined locations visited by an animal to which the device is attached allows for monitoring the locations visited by an animal, and the data relating to the locations visited by the animal also facilitates in determining the health and other issues of the animal.

Figure 3:
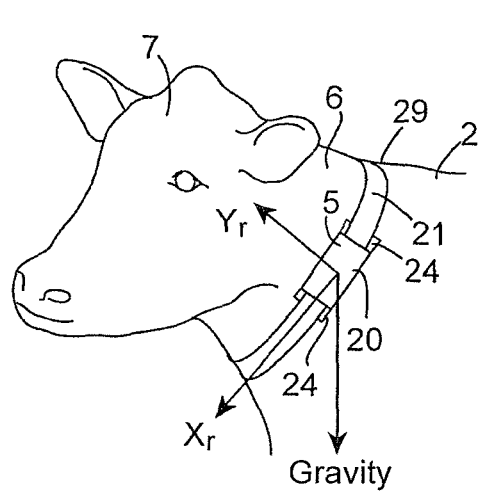
Figure 4:
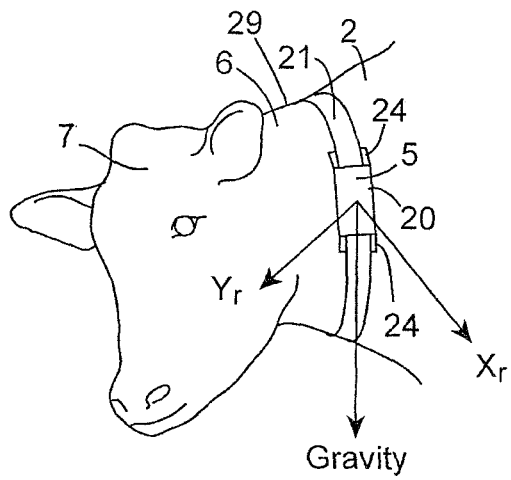
Figure 2:
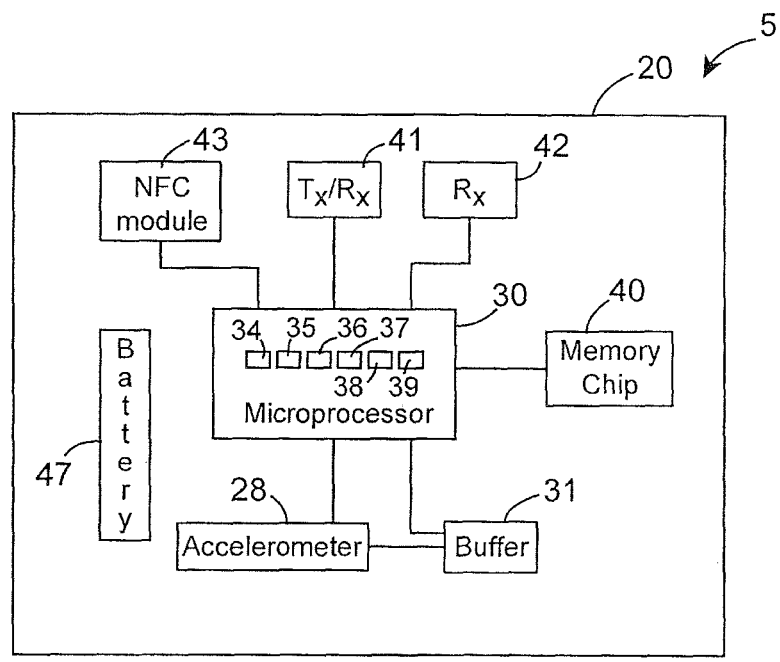
Figure 5A:
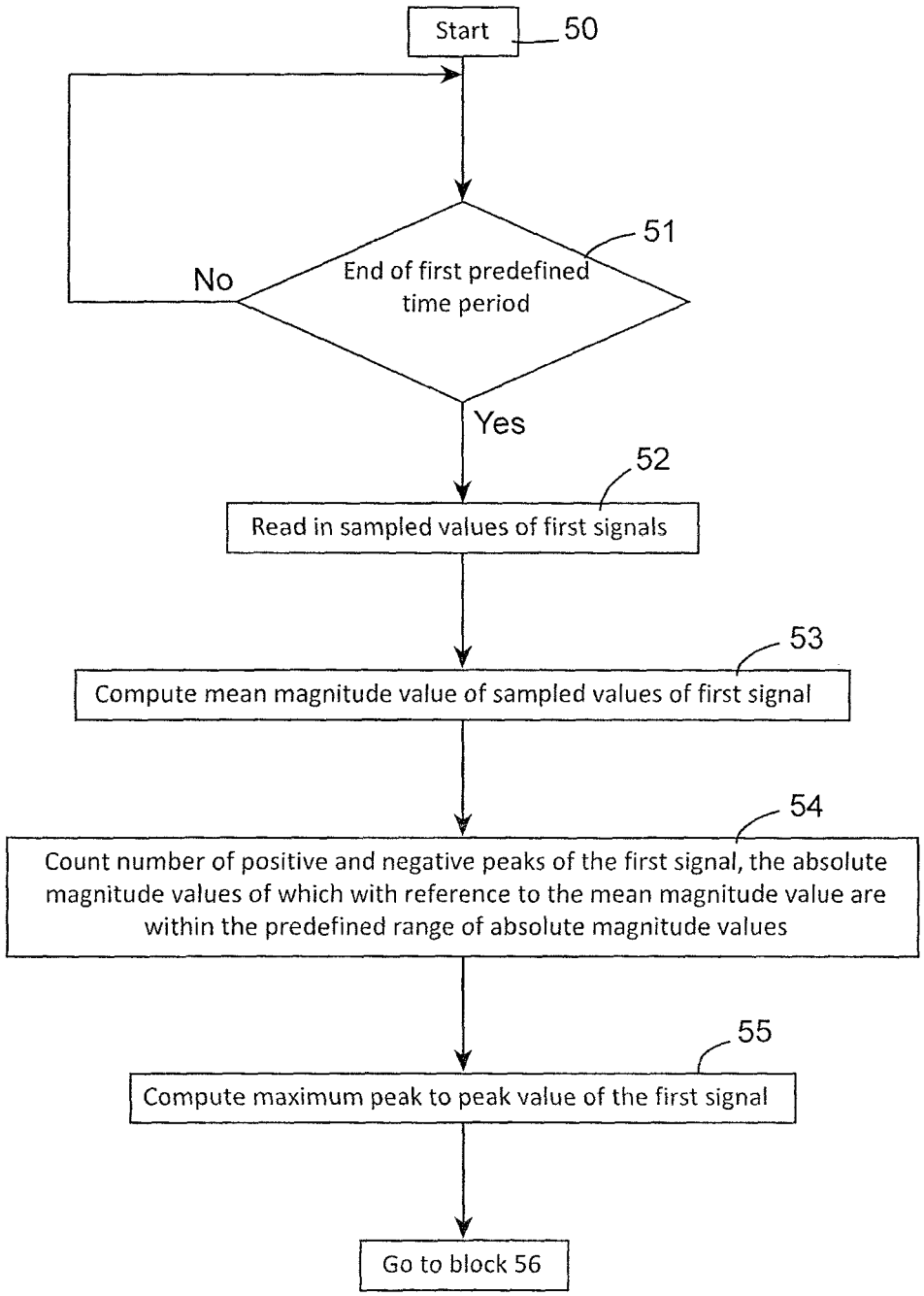
Figure 5B:
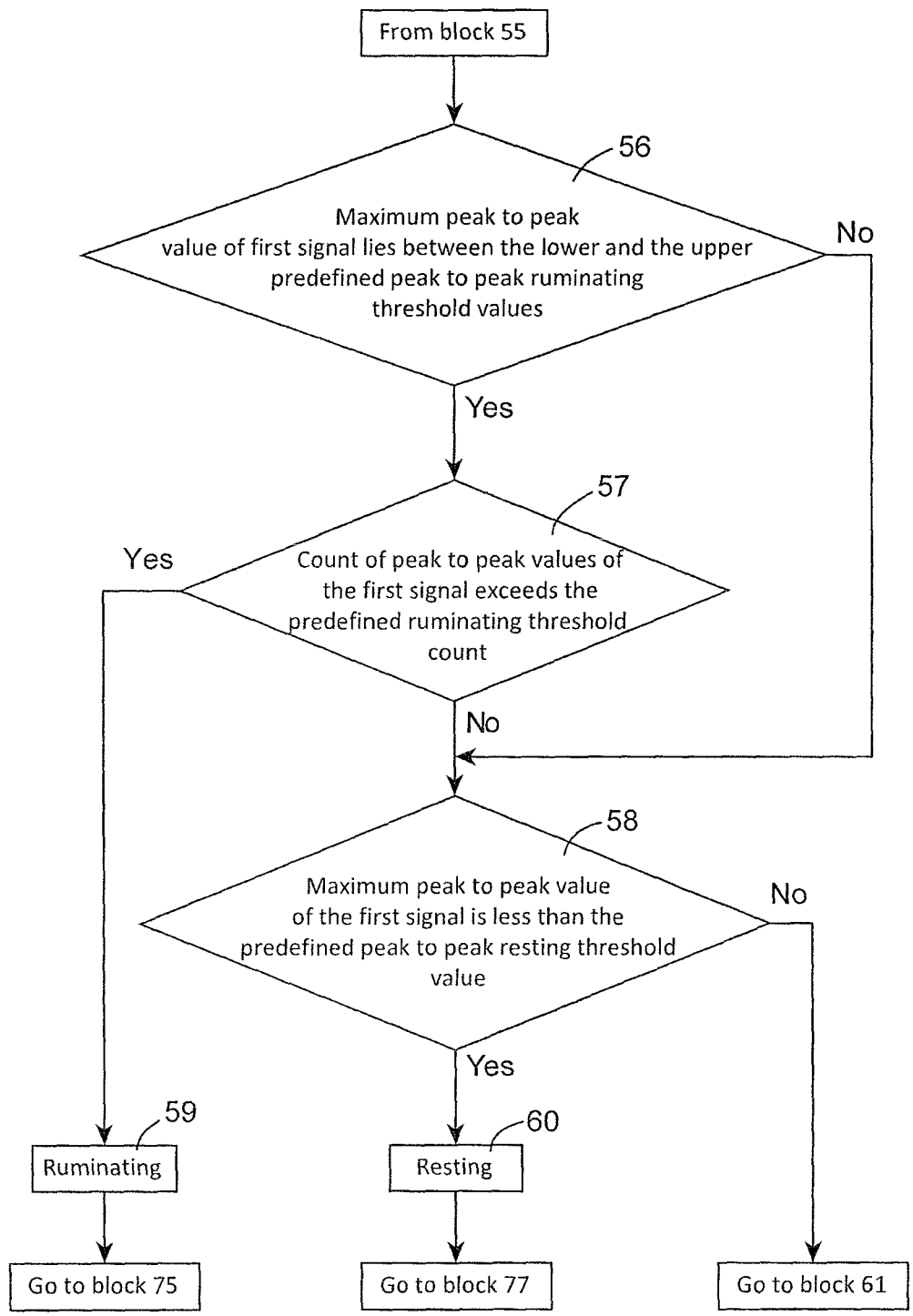
Figure 5C:
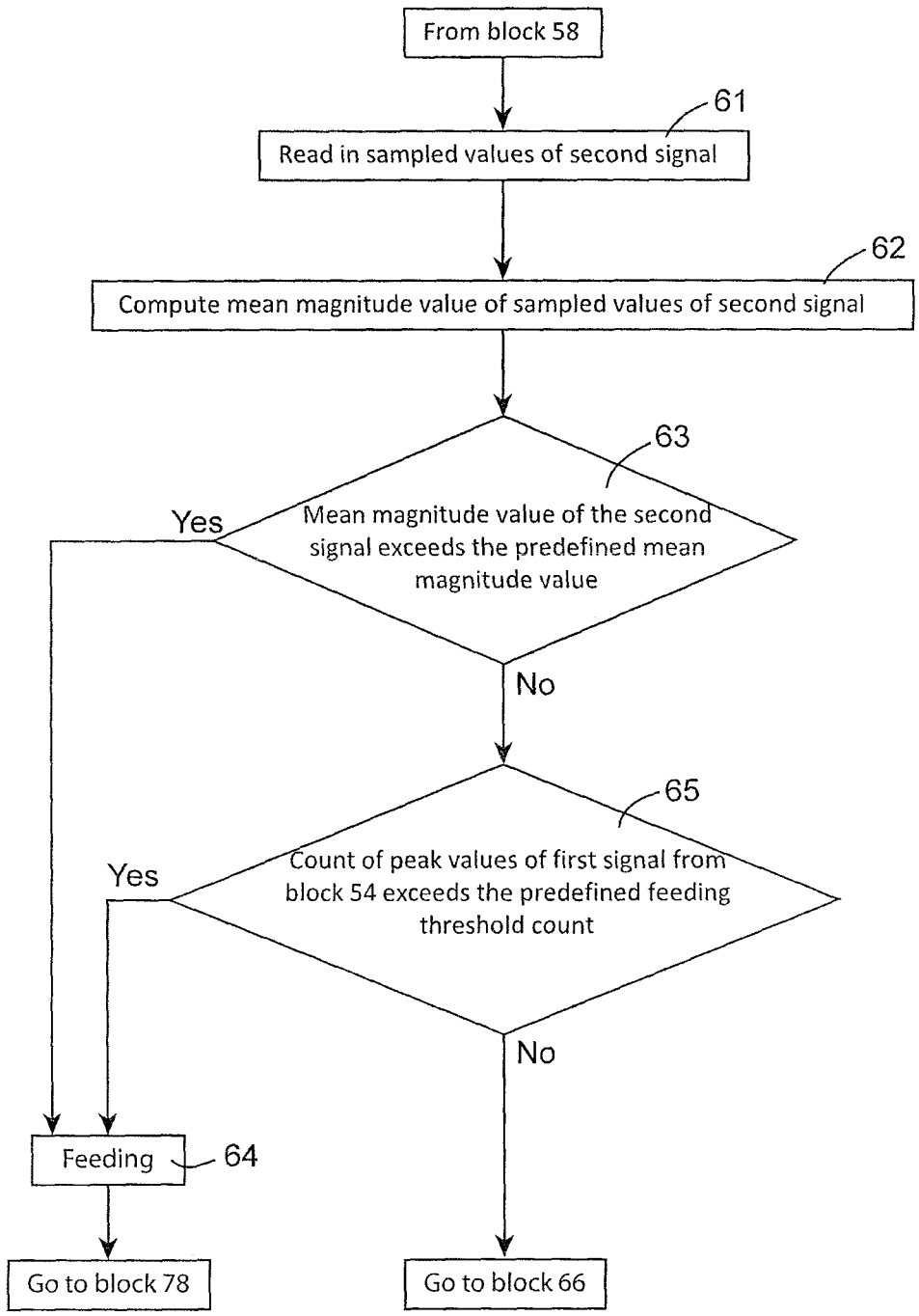
Figure 5D:
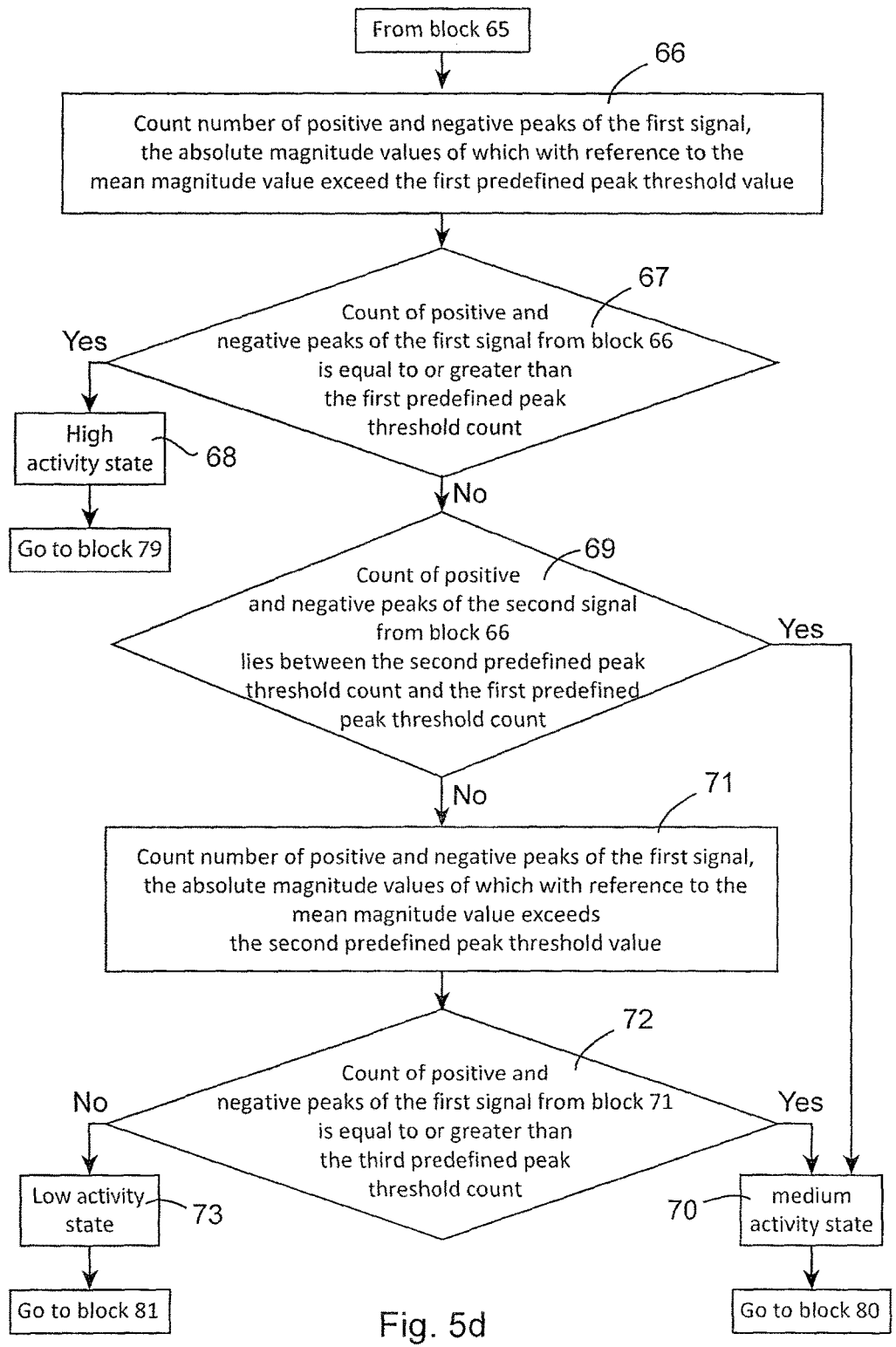
Figure 5E:
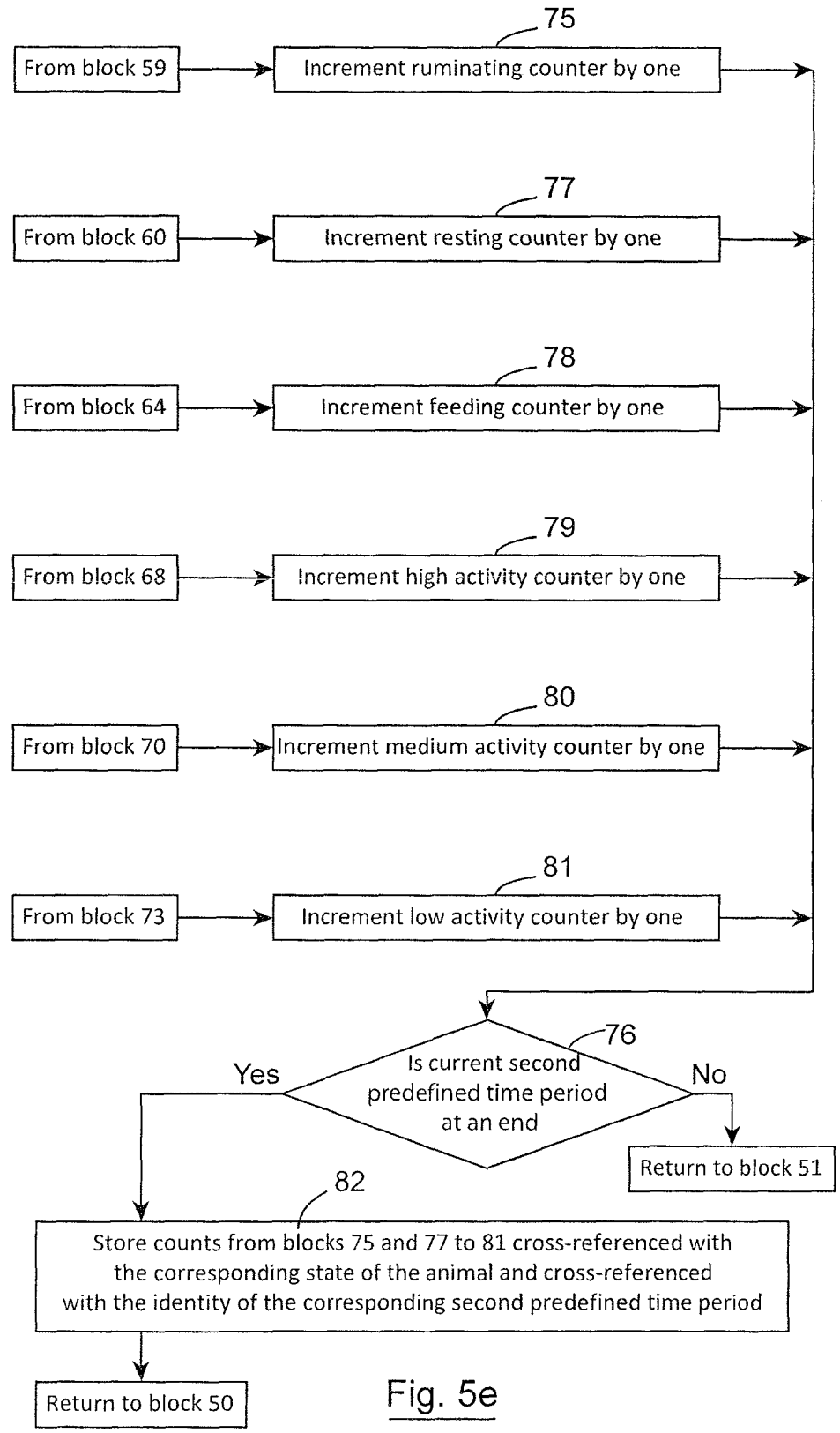

The invention will be more clearly understood from the following description of some preferred embodiments thereof, which are given by way of non-limiting examples, with reference to the accompanying drawings, in which:

FIG. 1 is a schematic view of a system according to the invention for detecting detectable states of an animal, FIG. 2 is a block representation of a device also according to the invention for detecting detectable states of an animal of the system of FIG. 1, FIG. 3 is a side elevational view of a portion of an animal with the device of FIG. 2 attached thereto, FIG. 4 is a side elevational view of a portion of the animal similar to FIG. 3 with the device attached to the animal, and with the portion of the animal in a different state to that of FIG. 3, FIGS. 5a to 5e are flowcharts of a routine carried out by the device of FIG. 2 for detecting detectable states of the animal, and FIGS. 6a to 6d are graphical representations of signals produced by the device of FIG. 2 and processed by the device of FIG. 2.

Referring to the drawings, there is illustrated a system according to the invention, indicated generally by the reference numeral 1, for determining detectable states of a plurality of animals 2, which in the case are cows, and may be dairy cows. In this embodiment of the invention the detectable states of the animals 2 include the states of ruminating, resting, feeding and active states, which include a state of high activity in which the animal is highly active, a state of low activity in which the level of activity of the animal is relatively low, but would be more active than if the animal were ruminating, resting or feeding, and a state of medium activity in which the level of activity of the animal is substantially midway between the state of high activity and the state of low activity. The system 1 comprises a plurality of devices also according to the invention, indicated generally by the reference numeral 5, for attaching to the animals, one device 5 being provided for each animal. In this embodiment of the invention the devices 5 are configured for attaching to the neck 6 of the animals 2 for detecting acceleration of the animals, and also for detecting the raised and lowered state of the head 7 of the animals. It has been found that by monitoring the acceleration of an animal and the raised and lowered states of the head of an animal, detectable states of an animal, such as ruminating, resting, feeding and active states can be detected as will be described in detail below.

The system 1 as well as comprising the devices 5 also comprises a remote computer 10, which may be a cloud computer server or alternatively may be a personal computer, a desktop computer, a laptop computer, a tablet computer or the like of a farmer. The computer 10 may also comprise a mobile smart phone, with computing capacity, or indeed, the computer 10 may comprise any other suitable computing device. In this embodiment of the invention the computer comprises a cloud computer server 10.

One or more relay stations 12 are located strategically around a field or fields in which the animals 2 are free to roam, or in an animal house or a milking parlour and the like in which the animals are housed or located. In general, a single relay station 12 would be provided adjacent a drinking trough or a milking parlour where the animals 2 would visit with known regularity. In this embodiment of the invention only one relay stations 12 is provided. The relay station 12 is configured to receive data transmitted by the devices 5, and to relay the transmitted data to the cloud computer server 10. The relay station 12 comprises a wireless transceiver 14 for transmitting and receiving data to and from the devices 5 as will be described below. A GSM module 15 is also located in the relay station 12 for communicating between the relay station 12 and the cloud computer server 10, and for relaying data received from the devices 5 to the cloud computer server 10, as also will be described below. The relay station 12 also comprises computing power to support and control the operation of the transmitter 14 and the GSM module 15, and to store data received from the devices 5 cross-referenced with the identity of the devices 5 for subsequent relaying to the cloud computer server 10. Such computing power may be provided by a microprocessor, a logic controller or any other computer or signal processor.

Turning now to the devices 5, and referring in particular to FIG. 2, each device 5 comprises a housing 20 which is adapted for securing to the neck 6 of the animal 2 by a ligature, namely, a strap 21 which extends around the neck 6 of the animal 2. The strap 21 is adapted for securing the device 5 to the neck 6 of the animal 2 with the housing 20 of the device 5 adjacent one side of the neck 6 of the animal 2 and also just behind the head 7 of the animal 2, as illustrated in FIGS. 1, 3 and 4, and with the device retained relatively tightly to the neck of the animal 5 so that the orientation of the housing 20 follows the orientation of the neck 6 of the animal 2, for a reason to be described below. Strap engaging brackets 24 are provided on the housing 20 through which the strap 21 is passed for securing the housing to the strap 21.

An acceleration sensor, which in this embodiment of the invention comprises a three-axis accelerometer 28 defining X, Y and Z axes, respectively, extending orthogonally relative to each other is located within the housing 20 of each device 5. The accelerometer 28 of each device is oriented in the housing 20 so that when the device 5 is attached to the neck 6 of the animal 2 by the strap 21, the Y-axis of the accelerometer extends substantially parallel to the back 29 of the neck 6 of the animal, and the X-axis extends substantially perpendicularly to the back 29 of the neck 6 of the animal 2 in a generally upwardly downwardly direction. The Z-axis of the accelerometer 28 extends substantially horizontally in a direction transversely of the neck 6 of the animal. As discussed above the device 5 is held relatively tightly to the neck 6 of the animal 2, so that the Y-axis of accelerometer 28 remains substantially parallel to the back 29 of the neck 6 of the animal, as the head of the animal is raised and lowered. Similarly, the X-axis of the accelerometer remains substantially perpendicular to the back of the neck of the animal as the animal raises and lowers its head.

The accelerometer 28 produces a first signal which is indicative of acceleration to which the accelerometer 28 is subjected along the X-axis, which in turn is indicative of acceleration of the head 7 and neck 6 of the animal 2, and which accordingly is indicative of the movement of the head 7 and neck 6 of the animal 2 as well as general motive movement of the animal. The accelerometer 28 produces a second signal which is indicative of acceleration to which the accelerometer 28 is subjected along the Y-axis, which in turn is indicative of the raised and lowered states of the head 7 of the animal 2. In this embodiment of the invention signals produced by the accelerometer 28, which are indicative of acceleration to which the accelerometer 28 is subjected along the Z-axis is not used, although it is envisaged that in some embodiments of the invention, as will be discussed briefly below, the third signal produced by the accelerometer 28 may be used.

A signal processor, in this embodiment of the invention a microprocessor 30 is located within the housing 20 of each device 5 and is programmed to continuously sample the first and second signals from the accelerometer 28 at a predefined sampling rate, which in this embodiment of the invention is approximately 11 Hz during consecutive first predefined time periods, each of approximately 11.5 seconds duration. As the sampled values of the first and second signals are read by the microprocessor 30, they are sequentially written into a buffer 31 during each first predefined time period. The buffer 31 is also located in the housing 20. At the end of each first predefined time period, the microprocessor 30 reads the sampled values of the first and second signals which were sampled during that first predefined time period from the buffer 31 and processes the read sampled values as will be described below. From the processed sampled values of the first and second signals which are processed at the end of each first predefined time period, the microprocessor 30 is configured to detect which of the states the animal had been in for that first predefined time period.

The microprocessor 30 is configured to form six counters for counting the numbers of first predefined time periods that the animal 2 is in the respective states of ruminating, resting, feeding, high activity, medium activity and low activity states during consecutive second predefined time periods. Each second predefined time period in this embodiment of the invention is of duration of 15 minutes. The counters are identified by the reference numerals 34 to 39 for counting the ruminating, resting, feeding, high activity, medium activity and low activity states, respectively. At the end of each second predefined time period the counts of the counters 34 to 39 are stored in a memory chip 40 located in the housing 20. The counts of the counters 34 to 39 are stored in the memory chip 40 cross-referenced with the times of the respective second predefined time periods.

An identifying code of the corresponding device 5 is stored in the memory chip 40, and data relating to the states of the corresponding animal 2 when being transmitted from the device 5 is cross-referenced with the identifying code of the device 5.

A communicating means, which in this embodiment of the invention comprises a wireless transceiver 41, a short range wireless receiver 42 and a wireless Near Field Communications module 43 are located in the housing 20 of each device 5. The transceiver 41 is adapted for two-way communications between the device 5 and the relay station 12, and transmits data indicative of the stored states of the corresponding animal 2 to the transceiver 14 of the relay station 12 in response to a wake-up signal received from the transceiver 14 of the relay station 12, when the animal 2 comes within range of the relay station 12, for subsequent transmission to the cloud computer server 10 through the GSM module 15. In this embodiment of the invention the wireless transceiver 41 is operable under the control of the microprocessor 30 in two power modes, namely, a low power mode for transmitting data to the relay station 12 in response to the wake-up signal from the relay station 12, when the animal and in turn the device 5 is within range of the relay station 12, and a high power mode for transmitting data to the transceiver 14 of the relay station 12 when the device is outside the normal range of the relay station.

The microprocessor 30 is configured so that on a wake-up signal from the relay station 12 being received by the transceiver 41 when the animal is within range of the relay station 12, the microprocessor 30 operates the transceiver 41 in the low power mode, and transmits data indicative of the states of the animal during the second predefined time periods stored in the memory chip 40 since the last transmission to the relay station 12 for subsequent relaying to the cloud computer server 10. The transceiver 41 is operable in the high power mode for transmitting data indicative of the states of the animal directly to the relay station 12 in response to the microprocessor 30 detecting from the processed data from the first and second signals that an emergency may exist in the state of the animal.

In order to minimise the energy requirement of the device 5, the microprocessor 30 is programmed only to transmit the data indicative of the states of the animal during the second predefined time periods stored in the memory chip 40 in response to the wake-up signal from the relay station 12 if the time which has elapsed since the last transmission of data indicative of the states of the animal during the second predefined time periods is greater than a predefined elapsed time period. In other words, after a transmission of the data indicative of the states of the animal during the second predefined time periods by the device 5, the microprocessor 30 commences timing the predefined elapsed time period, and during the timing of that predefined elapsed time period, the microprocessor 30 does not respond to any of the wake-up signals received from the relay station 12 until that predefined elapsed time period has timed out. Once the predefined elapsed time period has timed out, the microprocessor 30 is then responsive to the next one of the wake-up signal which it receives from the relay state and transmits the storage data indicative of the states of the animal during the second predefined time periods since the last transmission was made. The predefined elapsed time period may be of any suitable or desired duration, and typically would be of duration in the range of 1 hour to 12 hours, and more typically, would be of duration in the range of 4 to 8 hours.

It is envisaged in some embodiments of the invention the transceiver 41 may be of the type which operates in a single power mode only, and in which case, in general, the transceiver would be a relatively low power consumption transceiver, and would have a relatively short transmission and receiving range, although it is envisaged in certain cases that the transceiver 41 may have a relatively long transmission and receiving range. However, it is also envisaged that in certain cases, two wireless transceivers may be provided, one of which would have a relatively long transmission range, and a second transceiver which would have a relatively short transmission range, and would operate with a significantly lower power requirement than the transceiver with the relatively long transmission range.

The Near Field Communications module 43 is configured for two-way communications with a portable hand-held powered device, for example, a mobile smart phone 44 which is programmed for and is capable of communicating in a Near Field Communications protocol. The smart phone 44 is programmed with a software application, namely, an app, in order to facilitate two-way communications in the Near Field Communications protocol with the Near Field Communications module 43 and with the microprocessor 30. The communication range of the Near Field Communications module 43 is approximately 40 mm to 50 mm. The microprocessor 30 and the Near Field Communications module 43 are configured to facilitate programming and reprogramming of the microprocessor 30 through the Near Field Communications module 43 by the smart phone 44 operating under the control of the app. Additionally, the microprocessor 30 and the Near Field Communications module 43 are configured so that the identifying code of the device 5 which is stored in the memory chip 40 for identifying the device 5 can be read out of the memory chip 40 through the Near Field Communications module 43 and into the smart phone 44 to facilitate cross-referencing of the identifying code of the device 5 with an identifying code of the animal, which would identify the animal 2 to which the device 5 is attached. The identifying code of the animal may be, for example, the identification number of the animal by which the animal is identified by an ear tag or other suitable identifying tag. This enables the identity of the animal to be cross-referenced with the identifying code stored in the memory chip 40. The identifying code of the device 5 is cross-referenced with the identity of the cow in both the smart phone 44 and in the cloud computer server 10. Additionally, the smart phone 44 may store the identifying code of the device cross-referenced with the identity of the animal, and any other relevant data relating to the animal under the control of the app with which the smart phone 44 is programmed, such other data relating to the animal may be downloaded from the cloud computer server 10, or from a cloud database of the cloud computer server 10 in which such other data related to the animal is stored. The Near Field Communications module 43 is also configured so that data may be downloaded from and uploaded to the device 5 by the smart phone 44 under the control of the app with which the smart phone 44 is programmed. Such data which may be downloaded from the device 5 to the smart phone 44 may include the states of the animal cross-referenced with the corresponding second predefined time periods over a desired length of time, and also cross-referenced with the identifying code of the device 5 and the identifying code of the animal 2.

The wireless receiver 42 comprises an inductively coupled low frequency signal receiver coil which typically operates at 120 kHz to 140 kHz. The receiver 42 is provided for receiving identification signals from short range wireless transmitters 45 located at predefined locations 46 visited by the animal. The microprocessor 30 is programmed so that on reading an identification signal of a predefined location 46 received by the receiver 42 from the transmitter 45 at that location, the microprocessor 30 records the identity of the location 46 from the received identification signal, the time at which the identification signal is received, and the duration of reception of the identification signal. The identity of the location 46, the time of the visit to the location 46 by the animal and the duration of the visit by the animal to the location 46 is stored by the microprocessor 30 in the memory chip 40 for subsequent transmission through the transceiver 41 to the relay station 12, or through the Near Field Communications module 43. The transmitters 45 which are located at the predefined locations 46, for example, drinking troughs, feeding troughs and other locations to which a visit by the animal would be of interest are transmitters with a relatively short range, typically no more than a few metres, depending on the size and length of the drinking trough or feeding trough or other such location 46, as the case may be, and are configured to wirelessly and intermittently transmit an identification signal containing data identifying the corresponding predefined location 46 for reception by the receiver 42 of the device 5 when the animal 2 comes within range of the transmitter 45. Typically, the transmitters 45 transmit their respective identification signal at one-second intervals at a frequency in the range of 120 kHz to 140 kHz corresponding to the receiving frequency to which the receiver 42 is tuned.

The microprocessor 30 transmits the stored data relating to the locations visited by the animal, the times at which the locations were visited and the durations of each visit along with the data relating to the states of the animal during the relevant second predefined time periods to the relay station 12 for a subsequent relay to the cloud computer server 10.

A battery 47 powers the device 5.

The microprocessor 30 of each device 5 is configured by a software programme, a routine of which is illustrated in FIGS. 5a to 5e for detecting the state of the corresponding animal 2 at the end of each first predefined time period. The microprocessor 30 is configured by the routine of FIG. 5 of the software programme, so that at the end of each first predefined time period the sampled values of the first and second signals from the accelerometer 28 sampled during that first predefined time period are processed to firstly ascertain if the animal is ruminating. If the animal is found not to be ruminating, the sampled values of the first and second signals sampled during that first predefined time period are further processed to detect if the animal is resting. If the animal is found not to be ruminating or resting, the sampled values of the first and second signals are further processed by the microprocessor 30 to ascertain if the animal is feeding. If the animal is not detected as ruminating, resting or feeding, the sampled values of the first and second signals sampled during that first predefined time period are then further processed to ascertain if the animal is in one of the three activity states, namely, a state of high activity, a state of medium activity and a state of low activity, as will be described below.

Figure 6A:
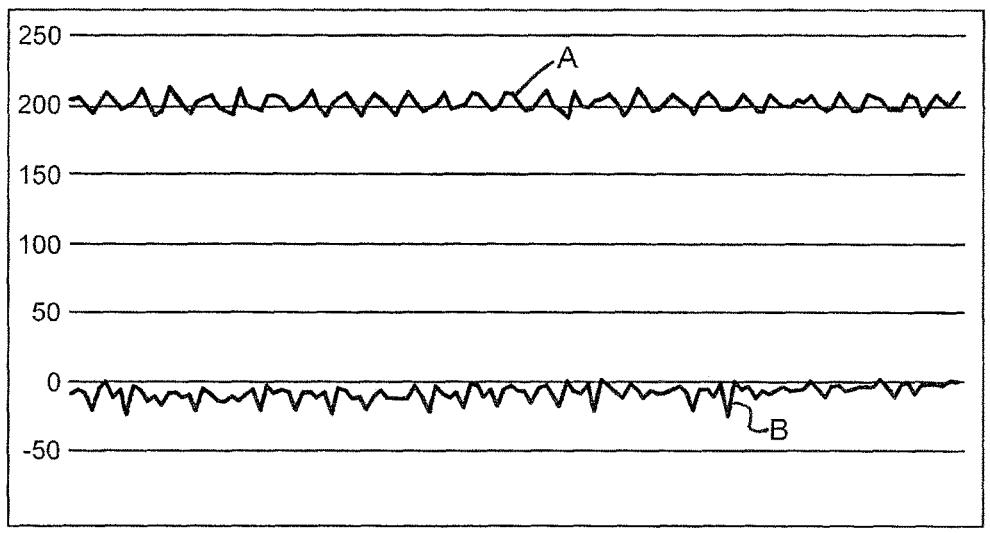
Figure 6B:
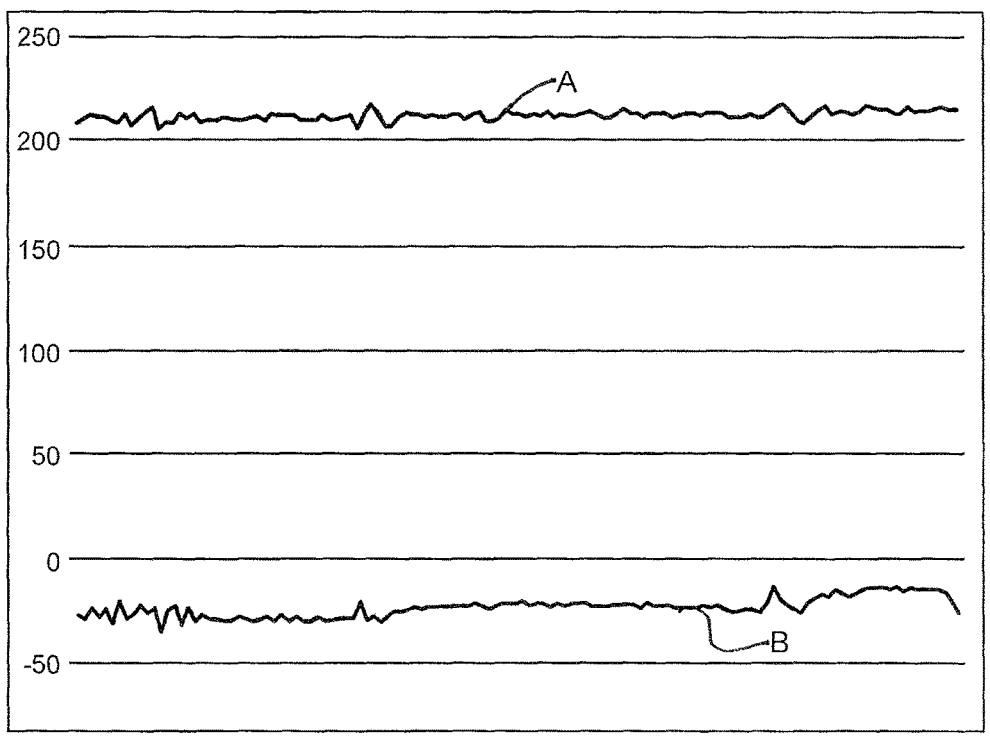
Figure 6C:
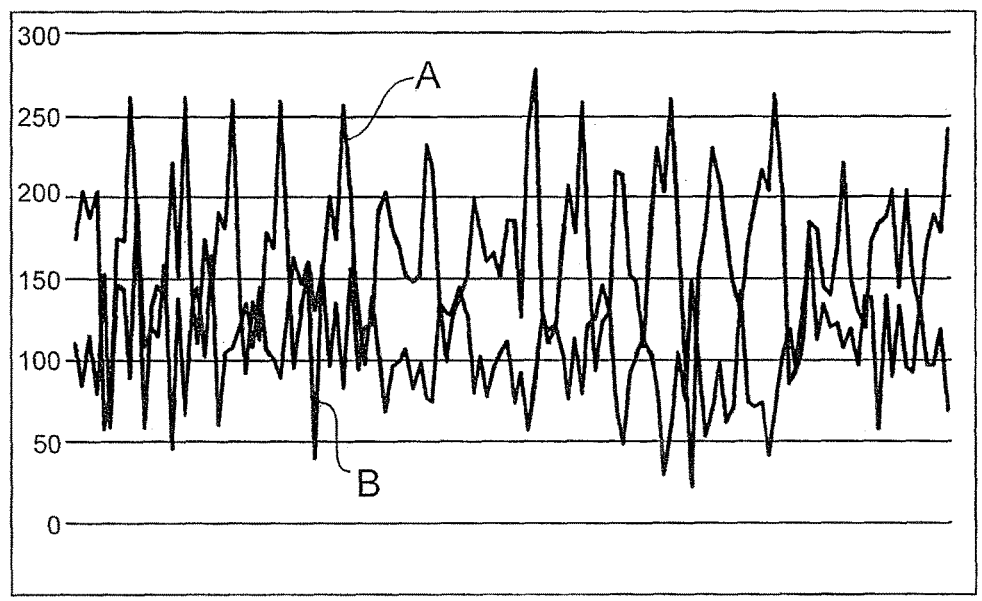
Figure 6D:
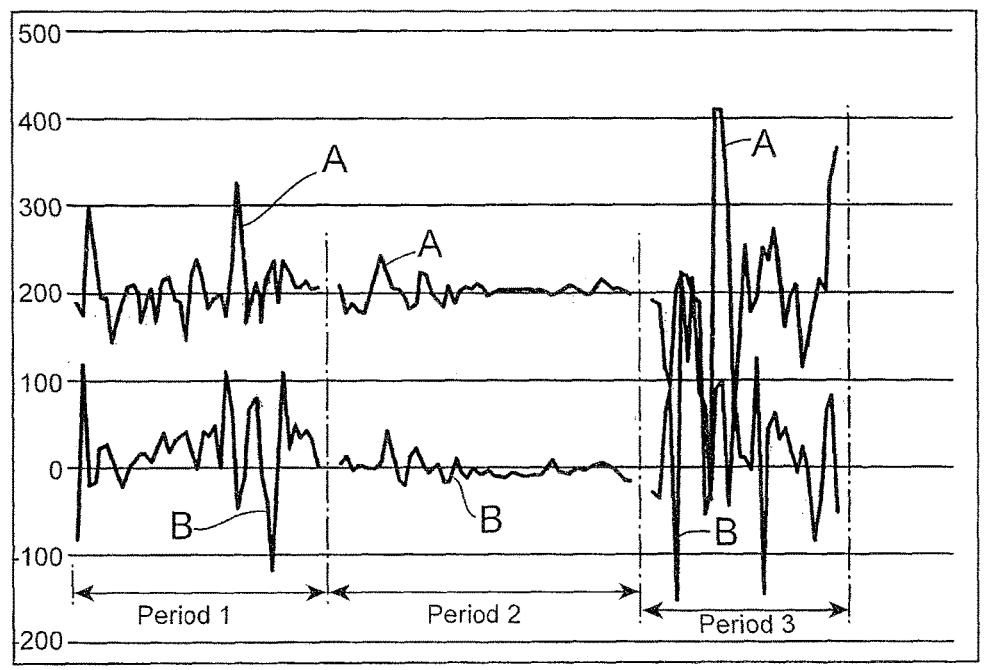

Graphical representations of the first and second signals sampled from the accelerometer 28 are illustrated by the graphs A and B, respectively, of FIGS. 6a to 6d, which illustrate the first and second signals during parts of different first predefined time periods. In FIGS. 6a to 6d time is plotted on the horizontal X-axis of the graphs. Acceleration to which the accelerometer 28 is subjected along its X-axis and Y-axis is plotted in arbitrary units on the vertical Y-axis of the graphs. In FIG. 6a the graphs A and B are typically representative of values of the first and second signals, respectively, which are indicative of an animal ruminating. In FIG. 6b the graphs A and B are typically representative of values of the first and second signals, respectively, which are indicative of an animal resting. In FIG. 6c the graphs A and B are typically representative of values of the first and second signals, respectively, which are indicative of an animal feeding. In FIG. 6d the graphs A and B are typically representative of values of the first and second signals, respectively, which are indicative of an animal in the three activity states. The parts of the graphs A and B of period 3 of FIG. 6d are indicative of an animal in a state of high activity, while the parts of the graphs A and B of period 1 are indicative of an animal in a state of medium activity, and the parts of the graphs A and B of period 2 are indicative of an animal in a state of low activity.

Turning now specifically to FIGS. 5a to 5e, block 50 starts the routine for detecting the state of the animal at the commencement of each second predefined time period of 11.5 seconds, and resets the counters 34 to 39 to zero. The routine then moves to block 51, which checks if the current first predefined time period has ended. If not, the routine returns to block 51. If block 51 determines that the current first predefined time period has ended, the routine moves to block 52. Block 52 reads the sampled magnitude values of the first signal from the buffer 31, which had been stored in the buffer 31 during the first predefined time period which has just ended, consecutively into the microprocessor 30. Block 53 computes a moving mean magnitude value of the magnitude of the sampled values of the first signal. Block 52 reads the sampled values of the first signal in blocks of sampled values, for example, in blocks of sampled values of from five to seven consecutive sampling points. During reading of the blocks of the sampled values of the sampling points of the first signal, the routine shuttles between blocks 52 and 53 to compute the mean magnitude value of the magnitude of the sampled values of the first signal for each of the blocks of sampled values of the first signal, in order that the computed mean magnitude value is a moving mean magnitude value.

On completion of the computation of the mean magnitude value of the sampled values sampled from the first signal during the just ended first predefined time period by block 53, block 53 also stores the computed mean magnitude value of the sampled values of the first signal for the just ended first predefined time period in memory of the microprocessor 30. On the mean magnitude value of the first signal being stored in the microprocessor 30 by block 53, the routine moves to block 54.

Block 54 counts the number of the positive and negative peaks of the sampled values of the first signal above and below the computed mean magnitude value of the sampled values of the first signal during the just ended first predefined time period, the absolute magnitude values of which with reference to the just computed mean magnitude value of the sampled values of the first signal are within a predefined range of absolute magnitude values. The upper and lower absolute magnitude values of the predefined range of absolute magnitude values are defined as respective functions of the computed mean magnitude value of the sampled values of the first signal for the just ended first predefined time period, and ideally, are defined as percentage values of the computed mean magnitude value of the sampled values of the first signals. The percentage values of the computed mean magnitude value which represent the upper and lower values of the predefined range of absolute magnitude values are dependent on the type of animal to which the device 5 is attached and also on the type of cow. It has been found that for a dairy cow when ruminating, typical absolute magnitude values of the positive and negative peaks of the sampled values of the first signal range between a lower absolute magnitude value of approximately 0.5% of the computed mean magnitude value of the first signal and an upper absolute magnitude value of approximately 10% of the computed mean magnitude value of the corresponding first signal for the first predefined time period.

Referring in particular to FIG. 6a, it can be seen from graph A, which represents a plot of the sampled values of the first signal during a part of one of the first predefined time period that the mean magnitude value of the sampled values of the first signal for that first predefined time period has been computed to be an arbitrary value of approximately 200 arbitrary units. In this embodiment of the invention a reading of 200 arbitrary units equates to one G force, namely, the acceleration due to gravity. This is the magnitude value of the first signal when the X-axis of the accelerometer 28 is extending substantially vertically, in other words, when the back 29 of the neck 6 of the animal 2 is extending substantially horizontally. Prior to counting the positive and negative peaks which lie within the predefined range of absolute magnitude values, block 54 computers the lower and upper absolute magnitude values of the predefined range of absolute magnitude values as 0.5% and 10%, respectively, of the computed mean magnitude value of the first signal, which had been computed by block 53 for the just ended first predefined time period.

Accordingly, since for the just ended first predefined time period block 53 computed the mean magnitude value to be 200 arbitrary units, block 54 for this just ended first predefined time period computes the lower and upper absolute magnitude values of the predefined range of absolute magnitude values as 1 arbitrary unit, and 20 arbitrary units, respectively, which are stored for this just ended first predefined time period in memory in the microprocessor 30. Block 54 then counts the number of positive and negative peaks, the absolute values of which lie between 1 arbitrary unit and 20 arbitrary units.

However, in general, it is envisaged that the lower absolute magnitude value of the predefined range of absolute magnitude values may lie from 0.1% to 1% of the computed mean magnitude value, while the upper absolute magnitude value of the predefined range of absolute magnitude values may lie in the range of 7% to 13% of the computed mean magnitude value, although the invention is not limited to any such ranges of lower and upper absolute magnitude values of the predefined range of absolute magnitude values, since as discussed above, the upper and lower absolute magnitude values of the predefined range of absolute magnitude values vary depending on the type of animal, and may also vary depending on the type of accelerometer.

On completing the count of the number of positive and negative peaks, the absolute magnitude values of which with reference to the computed mean magnitude value are within the predefined range of absolute magnitude values, block 54 stores the count of the number of the positive and negative peaks in the microprocessor 30 for the just ended first predefined time period.

The routine then moves to block 55. Block 55 computes the maximum peak to peak value of the sampled values of the first signal during the just ended first predefined time period as the sum of the absolute magnitude values of the maximum positive peak with reference to the mean magnitude value of the first signal, and the absolute magnitude value of the maximum negative peak with reference to the mean magnitude value of the first signal, in other words, the negative peak with the maximum absolute value with reference to the mean magnitude value. Block 55 then stores the computed maximum peak to peak value in memory of the microprocessor 30. The routine then moves to block 56.

Block 56 compares the computed maximum peak to peak value of the sampled values of the first signal with lower and upper predefined peak to peak ruminating threshold values.

The lower and upper predefined peak to peak threshold values are defined as functions of the computed mean magnitude value of the sampled values of the first signal during each first predefined time period, and in this embodiment of the invention are defined as respective percentage values of the computed mean magnitude value for each first predefined time period. It has been found that the lower and upper predefined peak to peak threshold values depend on the type of animal. It has also been found that in this embodiment of the invention for animals which are ruminating the maximum peak to peak value of the sampled values of the first signal does not fall below a lower peak to peak value in the range of 1% to 7% of the mean magnitude value of the sampled values of the first signal, and does not exceed an upper peak to peak value in the range of 16% to 22% of the mean magnitude value of the first signal. In this embodiment of the invention it has been found that for dairy cows when ruminating the maximum peak to peak value of the sampled values of the first signal lie within lower and upper peak to peak values of 4% and 19.5% respectively, of the mean magnitude value of the sampled values of the first signal. Accordingly, in this embodiment of the invention the lower predefined peak to peak ruminating threshold value is set at 4% of the computed mean magnitude value of the sampled values of the first signal and the upper predefined peak to peak ruminating threshold value is set at 19.5% of the mean magnitude value of the sampled values of the first signal for each first predefined time period. Since block 53 computed the mean magnitude value for this just ended first predefined time period to be 200 arbitrary units, block 56 computes the lower and upper predefined peak to peak ruminating threshold values for this first predefined time period as 8 arbitrary units and 39 arbitrary units, respectively, which are stored in memory of the microprocessor 30.

Block 56 then compares the maximum peak to peak value of the first signal computed by block 55 with the just computed lower and upper predefined peak to peak ruminating threshold values.

If block 56 determines that the maximum peak to peak value of the sampled values of the first signal during the just ended first predefined time period lies between the lower and upper predefined peak to peak ruminating threshold value, the routine moves to block 57. If block 56 determines that the maximum peak to peak value of the sampled values of the first signal is greater than the upper predefined peak to peak ruminating threshold value or less than the lower predefined peak to peak ruminating threshold value, the routine moves to block 58, which is described below.

Block 57 compares the count of the peak values determined by block 54 with a predefined ruminating threshold count. The predefined ruminating threshold count is predefined and stored in the microprocessor 30. It has been found that during any one of the first predefined time periods of 11.5 seconds when a dairy cow is ruminating, the count of positive and negative peak values determined by block 54 would not be less than fifty peaks, and in this embodiment of the invention the predefined ruminating threshold count is set and stored in the microprocessor 30 as a count of fifty. However, it will be appreciated that the predefined ruminating threshold count may vary upwardly or downwardly from fifty, depending on the animal, and indeed, the type of cow. Needless to say, the predefined ruminating threshold count will vary depending on the duration of first predefined time period. However, for a first predefined time period of 11.5 seconds, the count of positive and negative peak values of the sampled values of the first signal determined by block 54 for a ruminating dairy cow will exceed fifty. However, the invention is not to be limited to a predefined ruminating threshold count of fifty peaks.

If block 57 determines that the count of peak to peak values determined by block 54 exceeds the first predefined ruminating threshold count, the routine moves to block 59. Block 59 detects that the animal is ruminating and moves to block 75, which is described below. If block 57 determines that the count of positive and negative peak values, the absolute magnitude values of which with reference to the mean magnitude value are within the predefined range of absolute magnitude values, which is computed by block 54, does not exceed the predefined ruminating threshold count of fifty, the subroutine moves to block 58.

While the mean magnitude value of the first signal for the just ended first predefined time period of FIG. 6a has been computed by block 53 as being 200 arbitrary units for this example of ruminating, the mean magnitude value of the first signal may be of other values besides 200 arbitrary units during ruminating of an animal.

Block 58 compares the maximum peak to peak value of the sampled values of the first signal computed by block 55 with a predefined peak to peak resting threshold value. It has been found that if the count of positive and negative peak values, the absolute magnitude value of which with reference to the mean magnitude value are within the first predefined range of absolute magnitude values as determined by block 54 does not exceed the predefined ruminating threshold count of fifty, it is possible that the animal is resting. It has also been found that if the maximum peak to peak value of the sampled values of the first signal does not exceed the predefined peak to peak resting threshold value, the animal would be resting. The predefined peak to peak resting threshold value varies from type of animal to type of animal, and indeed, from type of cow to type of cow. In this embodiment of the invention the predefined peak to peak resting threshold value is defined as a function of the computed mean magnitude value of the sampled values of the first signal during each first predefined time period, and preferably, is defined as a percentage value of the computed mean magnitude value of the sampled values of the first signal during each first predefined time period. It has been found that in a resting animal the maximum peak to peak value of the sampled values of the first signal will not exceed 30% of the computed mean magnitude value. In this embodiment of the invention it has been found that the maximum peak to peak value of the sampled values of the first signal do not exceed a predefined value of 20% of the computed mean magnitude value for a resting dairy cow. Since block 53 computed the mean magnitude value at 200 arbitrary units block 58 computes the predefined peak to peak resting threshold value to be 40 arbitrary units which is stored in memory in the microprocessor 30. Block 58 then compares the maximum peak to peak value of the first signal computed by block 55 with the computed predefined peak to peak resting threshold value.

Accordingly, if block 58 determines that the maximum peak to peak value computed by block 55 does not exceed the predefined peak to peak resting threshold value, the routine moves to block 60, which determines that the animal is resting. The routine is then moved to block 77, which is described below. If block 58 determines that the maximum peak to peak value of the sampled values of the first signal computed by block 55 during the just ended first predefined time period does exceed the predefined peak to peak resting threshold value, the routine moves to block 61.

Graph A of FIG. 6b is a part of a typical graph representing the first signal from another first predefined time period of a resting animal. As can be seen from graph A of FIG. 6b block 53 would have computed the mean magnitude value of the sampled values of the first signal of graph A to be in the order of 210 arbitrary units. Block 54 would have computed the lower and upper absolute magnitude values of the predefined range of absolute magnitude values based on the computed mean magnitude value of 210 arbitrary units. Block 54 would then have counted the number of positive and negative peaks of the first signal which were within that predefined range of absolute magnitude values. Block 55 would have computed the maximum peak to peak value of the first signal based on the computed mean magnitude value of 210 arbitrary units. In processing the sampled values of the first signal of graph A through blocks 56 and 57 the microprocessor would have detected that the animal was not ruminating. The routine would then have moved to block 58 which would have computed the predefined peak to peak resting threshold value based on the computed mean magnitude value of 210 arbitrary units, and block 58 would have determined that the maximum peak to peak value of the first signal of graph A of FIG. 6*b* was less than computed predefined peak to peak resting threshold value, and the routine would have moved to block 60, which would have detected that the animal was resting.

Returning now to block 61, block 61 reads into the microprocessor 30 the sampled magnitude values of the second signal consecutively from the buffer 31, which had been stored in the buffer 31 during the first predefined time period which has just ended. The reading in of the sampled magnitude values of the second signal from the buffer 31 to the microprocessor 30 may be carried out at any suitable stage in the routine, either at this stage, or earlier in the routine, for example, before or after the reading of the sampled magnitude values of the first signal into the microprocessor 30. The routine then moves to block 62, which computes the mean magnitude value of the sampled magnitude values of the second signal, and the routine moves to block 63.

Block 63 compares the mean magnitude value of the sampled values of the second signal which has been computed by block 62 with a predefined mean magnitude value to ascertain the raised or lowered state of the head of the animal. The value of the second signal when the back 29 of the neck of the animal 2 is extending substantially horizontally is zero arbitrary units, since the second axis of the accelerometer 28 would also be extending substantially horizontally. It has been found in this embodiment of the invention that with the monitoring device 5 attached to the neck 6 of an animal, with the second axis of the accelerometer extending substantially parallel to the back of the neck of the animal, when the head of the animal is in a lowered state sufficient for grazing or feeding from a ground level trough, the mean magnitude value of the second signal should be greater than 60 arbitrary units. Accordingly, in this embodiment of the invention the predefined mean magnitude value of 60 arbitrary units is stored in the microprocessor 30. Accordingly, if block 63 determines that the mean magnitude value of the second signal computed by block 62 exceeds the predefined mean magnitude value of 60 arbitrary units, the routine moves to block 64, which detects the animal as feeding. The routine then moves to block 78, which is described below.

Referring now to FIG. 6*c*, graphs A and B of FIG. 6*c* are parts of typical graphs of the first and second signals, respectively of a part of another first predefined time period in which the animal is feeding. Block 53 would have computed the mean magnitude value of the second signal, namely, graph B of FIG. 6*b* to have a mean value greater than 100 arbitrary units, which is greater than the predefined mean magnitude value of 60 arbitrary units of the second signal, and thus, block 63 would have determined the mean magnitude value of the second signal to have exceeded the predefined mean magnitude value of 60 arbitrary units, and the routine would have moved to block 64 and determined that the animal was feeding.

If however block 63 determines that the mean magnitude value of the second signal computed by block 62 is less than the predefined mean magnitude value, indicating that the head of the animal is either raised above a normal grazing level, or at a level at which the head of the animal would be if feeding from a ground level trough, the routine moves to block 65.

Block 65 compares the count of positive and negative peak values of the first signal, the absolute magnitude values of which with reference to the mean magnitude value of the first signal are within the first predefined range of absolute magnitude values, which has already been determined by block 54, with a predefined feeding threshold count. It has been found that in certain cases, an animal can be feeding even when the head of the animal is not in the lowered state. For example, in certain feeding systems, particularly those used in intensive rearing of animals, the animal feed is presented to the animal at a level at which the head of the animal could be in a raised state. Accordingly, block 65 is provided to detect such feeding. It has been found that if the maximum peak to peak value of the first signal which is computed by block 55 exceeds the predefined resting threshold value, the animal could be feeding. It has also been found that if the count of positive and negative peak values of the first signal as determined by block 54 exceeds a predefined feeding threshold count, the animal would be feeding. In this embodiment of the invention the predefined feeding threshold count is similar to the predefined ruminating threshold count for each first predefined time period, and thus, in this case the predefined feeding threshold count is also stored in memory of the microprocessor 30 as fifty. However, as discussed above with reference to the predefined ruminating threshold count, the predefined feeding threshold count is also dependent on the duration of the first predefined time period, and may also vary depending on the type of animal. It will also be appreciated that the predefined feeding threshold count and the predefined ruminating threshold count may be different for some animal.

Accordingly, if block 65 determines that the count of the positive and negative peak values of the first signal computed by block 54 exceeds the predefined feeding threshold count of fifty, the routine moves to block 64, which as discussed above, detects that the animal is feeding. If block 65 determines that the count of the positive and negative peak values of the first signal computed by block 54 does not exceed the predefined feeding threshold count of fifty, the routine moves to block 66.

At this stage, the animal has been determined as being neither ruminating, resting nor feeding. Thus, the only other state of the animal would be an active state. In this embodiment of the invention the routine is configured to identify three active states of the animal, namely, a high activity state, a medium activity state, and a low activity state.

Block 66 counts the number of positive and negative peaks of the sampled values of the first signal of the just ended first predefined time period, the absolute magnitude values of which with reference to the mean magnitude value exceeds a first predefined peak threshold value. The reason for counting the number of positive and negative peaks, the absolute magnitude values of which with reference to the computed mean magnitude value exceed the first predefined peak threshold value is to determine if the animal is in a high activity state. It has been found that when an animal is in a state of high activity, the absolute magnitude value of a number of the positive and negative peaks of the sampled values of the first signal during each first predefined time period will exceed a first predefined peak threshold value, which will vary depending on the type of animal, and indeed on the type of cow.

The first predefined peak threshold value is defined as a function of the computed mean magnitude value of the sampled values of the first signal during each first predefined time period. Preferably, the first predefined peak threshold value is defined as a percentage value of the computed mean magnitude value. It has been found that in an animal in a state of high activity, a number of the positive and negative peaks of the sampled values of the first signal during each first predefined time period will be greater than 30% of the computed mean magnitude value. In this case, it has been found that for a dairy cow in a state of high activity, the absolute magnitude value of many of the positive and negative peak values of the sampled values of the first signal will be greater than 35% of the computed mean magnitude value. Accordingly, in this case, for each first predefined time period the first predefined peak threshold value is computed by block 66 to be 35% of the computed mean magnitude value and stored in the microprocessor 30. From the graph A of FIGS. 6a to 6d, 350 arbitrary units represents a value of approximately 35% of the computed mean magnitude value, namely, 70 arbitrary units, and this value for the first predefined peak threshold value is stored in memory in the microprocessor for this just ended first predefined time period.

On completion of the count by block 66, the routine moves to block 67. Block 67 checks if the count of the positive and negative peaks from block 66 is greater than or equal to a first predefined peak threshold count. The first predefined threshold count is predefined and stored in the microprocessor 30, and is dependent on the duration of the first predefined time period, and also on the type of animal, and in the case of cows on the type of cow. In general, it has been found that for a first predefined time period of 11.5 seconds, if the count of the positive and negative peak values determined by block 66 is greater than or equal to a first predefined peak threshold count of three, then the animal is in a state of high activity. Accordingly, the first predefined peak threshold count is set and stored in the microprocessor 30 at three. If block 67 determines that the count of the positive and negative peaks from block 66 is greater than or equal to the first predefined peak threshold count of three, the routine moves to block 68, which detects the animal as being in a state of high activity, and the routine moves to block 79, which is described below. If block 67 determines that the count of the positive and negative peak values of the first signal of block 66 is not greater than or equal to the first predefined peak threshold count of three, the subroutine moves to block 69.

Referring now to FIG. 6d, which as discussed above illustrates graphs A and B which are representative of first and second signal, respectively, for parts of three different first predefined time periods. Graph A of FIG. 6d during period 3 is a typical representation of the first signal for an animal in a state of high activity.

As can be seen block 53 would have computed the mean magnitude value of the sample values of FIG. 1 for graph A of the third period of FIG. 6d to be 200 arbitrary units, and as can be seen there are at least three peaks of the positive and negative peak which exceed the first predefined peak threshold value which would have been computed based on the computed mean magnitude value of 200 arbitrary units, which would have produced a first predefined peak threshold value of 70 arbitrary units. Thus, in this first predefined time period, block 67 would have moved the subroutine to block 68 which would detect the animal as being in the high activity state.

Returning now to block 69, block 69 checks if the count of positive and negative peaks of the first signal from block 66 lies between a second predefined peak threshold count and one less than the first predefined peak threshold count. In this case, the second predefined peak threshold count is one, and block 69 checks if the count of positive and negative peaks of the first signal from block 66 is one or two. It has been found that an animal is in a state of medium activity if the count of the positive and negative peaks of the first signal from block 66 lies between one and one less than the first predefined peak threshold count. If block 69 determines that the count of the positive and negative peaks of the first signal from block 66 is equal to one or two, the routine moves to block 70, which detects the animal as being in a state of medium activity. The routine then moves from block 70 to block 80, which will be described below.

If block 69 determines that the count of the positive and negative peaks of the first signal from block 66 is not equal to one or two, the routine moves to block 71, in order to determine if the animal could still be in a state of medium activity based on alternative parameters to those applied in block 69.

Block 71 counts the number of positive and negative peaks of the sampled values of the first signal sampled during the just ended first predefined time period, the absolute magnitude values of which with reference to the mean magnitude value exceeds a second predefined peak threshold value. It has been found that an animal would also in a state of medium activity, if the absolute magnitude of a number of the positive and negative peaks of the first signal were greater than a second predefined peak threshold value, which is defined as a function of the computed mean magnitude value, and preferably as a percentage of the computed mean magnitude value. It has been found that an animal is also in a medium active state if the absolute magnitude values of a number of the positive and negative peaks of the samples values of the first signal are greater than a second predefined peak threshold value of 10% of the computed mean magnitude value of the first signal. However, this value of the second predefined peak threshold value depend on the type of animal and in the case of cows, on the type of cows.

In the just ended first predefined time period of FIG. 6a, the computed mean magnitude value computed by block 53 is computed as 200 arbitrary units, block 71 computes the second predefined peak threshold value for this just ended predefined time period of FIG. 1 to be 20 arbitrary units. Block 71 then counts the number of positive and negative peaks of the sampled values of the first signal during the just ended first predefined time period, the absolute magnitude peak values exceed 20 arbitrary units.

On completion of the count by block 71, the routine moves to block 72, which checks if the count of the positive and negative peak values of the first signal counted by block 71 is greater than or equal to a third predefined peak threshold count. The third predefined peak threshold count will vary from animal to animal and indeed from cow to cow, and also will vary depending on the duration of the first predefined time period. However, in this case, it has been found that a third predefined peak threshold count of 12 would indicate that an animal is in a state of medium activity. In this embodiment of the invention the third predefined peak threshold count is computed and stored at a value of 12 in the microprocessor 30.

If block 72 determines that the count of the positive and negative peaks computed by block 71 is greater than or equal to the third predefined peak threshold count, the routine moves to block 70, which as already described, detects the animal as being in a medium active state.

In the event that block 72 determines that the count of the positive and negative peak values counted by block 71 is not greater than or equal to the third predefined peak threshold count, the routine moves to block 73, which detects the animal as being in a state of low activity. The routine then moves to block 81, which will be described below.

Referring again to FIG. 6d, graph A of period 1 of FIG. 6d represents a first signal of a part of another first predefined time period in which the animal is in a state of medium activity. In the first predefined time period of the first period of FIG. 6d block 53 would have computed a mean magnitude value of the sample values of the first signal to be in the order of 200 arbitrary units. 35% of the mean magnitude value of 200 units would have been 70 units, and 10% of the mean magnitude value would have been 20 units. Thus, in this case the first predefined peak threshold value would have been computed to be 70 arbitrary units, and the second predefined peak threshold value would have been computed to be 20 arbitrary units. In graph A of period 1 of FIG. 6d the graph includes two peaks which exceed 70 arbitrary units, and 12 peaks which exceed 20 arbitrary units. Accordingly, under both criteria, namely, that of block 69 and 72 the animal would have been detected as being in a state of medium activity during the first predefined time period of period 1 of FIG. 6d. However, it is to be understood that once either block 69 or block 72 detect that the animal is in a state of medium activity the animal is deemed to be in the state of medium activity.

Turning now to block 75, block 75 increments the counter 34 by one, which counts the number of first predefined time periods during each second predefined time period during which the animal is ruminating. The routine then moves to block 76, which is described below.

Turning now to block 77, block 77 increments the counter 35 by one, which counts the number of first predefined time periods during the second predefined time period that the animal is detected as being in a resting state. The routine then moves to block 76, which has already been described.

Turning now to block 78, block 78 increments the counter 36 by one, which counts the number of first predefined time periods that the animal has been detected as feeding during the second predefined time period. The routine then moves to block 76, which has already been described.

Turning now to block 79, block 79 increments the counter 37 by one, which counts the number of first predefined time periods during the second predefined time period that the animal is in the state of high activity. The routine then moves from block 76, which has already been described.

Turning now to block 80, block 80 increments the counter 38 by one, which counts the number of first predefined time periods during the second predefined time period that the animal is in a state of medium activity. The routine then moves to block 76, which has already been described.

Turning now to block 81, block 81 increments the counter 39 by one, which counts the number of first predefined time periods in which the animal has been detected in a state of low activity during the second predefined time period. The routine then moves to block 76, which has already been described.

Turning now to block 76, block 76 checks if the current second predefined time period has ended. If block 76 determines that the current second predefined time period has ended, the routine moves to block 82. Block 82 stores the counts from blocks 75 and 77 to 81, which are the counts in the counters 34 to 39 at the end of that second predefined time period. Block 82 stores the counts of the counters 34 to 39 cross-referenced with the corresponding states of the animal during that second predefined time period, and cross-referenced with the identity of the corresponding second predefined time period. Block 82 then returns the routine to block 50. If, however, block 76 determines that the current second predefined time period has not yet ended, block 76 returns the routine to block 51.

Turning now to the recovery of data from each device 5. In normal operation of the devices 5, no data is transmitted by the devices 5 until the animal 2 to which the device 5 is attached comes within range of the relay station 12. On receiving a wake-up signal from the transceiver 14 of the relay station 12 through the transceiver 41 of the device 5, the microprocessor 30 of that device operates the transceiver 41 in the low power mode, and transmits through the transceiver 41 the stored data relating to the states of the animal 2 during each one of the second predefined time periods, and the number of the first predefined time periods the animal 2 was in each of those states for each of the second predefined time periods since the last transmission of data from the device 5 occurred. Additionally, the stored data since the last transmission relating to the identity of the respective locations visited by the animal, the times at which the visits took place, and the duration of the respective visits is also transmitted by the device 5 through the transceiver 41 along with the data relating to the states of the animal. The transmitted data is received by the transceiver 14 of the relay station 12, which in turn relays the data to the cloud computer server 10 through the GSM module 15.

Prior to transmission from the device 5 the data is packaged for transmission by the microprocessor 30 into data packets, with the data packets comprising the identifying code of the device 5 stored in the memory chip 40 along with the data relating to the states of the animal 2 and the locations visited by the animal 2. Typically the relay station 12 will be located at a location which will be visited by the animals at least twice per day, so that the stored data relating to each animal in the corresponding device 5 will be transmitted to the relay station 12, and in turn relayed to the cloud computer 10 at least twice per day.

In the event that a period greater than a predefined time period of, for example, fifteen hours has elapsed since the last transmission from any one of the devices 5 has been received by the cloud computer server 10, the cloud computer server 10 through the GSM module 15 requests the relay station 12 to transmit a wake-up signal identifying that device 5 of sufficient strength to be received by the transceiver 41 of that device 5, in order to activate the microprocessor 30 of that device 5 to transmit the stored data relating to the states of the animal and the locations visited by the animal since the last transmission from that device 5 was made. On receipt of the wake-up signal, the microprocessor 30 of that device 5 operates the transceiver 41 in the high power mode, and transmits through the transceiver 41 the stored data relating to the states of the animal 2 during each one of the second predefined time periods and the stored data relating to the locations visited by the animal 2 since the last transmission of data from that device 5 was made. On receipt of the transmitted data by the relay station 12 the received data is relayed to the cloud computer server 10 by the relay station 12 through the GSM module 15.

By operating the transceiver 41 in the low power mode for transmissions of data to the relay station 12 when the devices 5 are within range of the relay station 12, significant power saving is achieved both in the devices 5 and the relay station 12, and in particular in the devices 5. Accordingly, provided that the interval between transmissions of data indicative of the states of the animal made by the devices 5 to the relay station 12, and in turn to the cloud computer server 10 are less than the predefined time periods of, for example, fifteen hours, the transmissions of the data indicative of the states of the animal 2 are made with the transceiver 41 operating in the low powered mode.

In the event that the microprocessor 30 determines that during a number of consecutive second predefined time periods the state of the animal has remained in a state of high activity, which could be indicative of the onset of oestrus, or over an abnormally long period of time the animal has remained in a resting state, which could be indicative of an injured or an ill animal, the microprocessor 30 is programmed to operate the transceiver 41 in the high powered mode and to output an alert signal through the transceiver 41 for reception by the relay station 12 for relaying to the cloud computer server 10. The alert signal includes the identifying code of the device 5 together with a signal alerting to the continuous highly active state or the continuous resting state of the animal.

Turning now to the cloud computer server 10. The cloud computer server 10 is programmed to determine various health states of the animal 2, for example, the onset of oestrus, which would be determined by comparing the high activity state of the animal 2 to historical activity states of the animal 2 and to the activity states of other animals in the same herd or group of animals, which are in a similar environment to that of that particular animal 2. In the event of the animal being in the state of high activity greater than its normal active state and being greater than the state of high activity of the other animals in the herd or group, then the onset of oestrus could be determined, as could other reproductive issues, for example, cystic ovarian diseases. Lameness or other injuries or illnesses would be determined in the case of an animal resting for excessively long time periods. Lack of ruminating and/or feeding of an animal would indicate an animal as being in poor health.

The data relating to the identity of the locations visited by each animal, the times of the visits and the durations of the visits is also processed by the cloud computer server 10 to also identify the health state of the animal. For example, if an animal has not visited a drinking trough for an extended period, this could also be an indication of ill health of the animal. If an animal is found not to have visited a feeding trough, for example, where nutrients in concentrated form are provided for the animals, corrective action could be taken to ensure that that particular animal received appropriate nutrients.

In use, each animal 2 of a herd or group of animals is provided with one of the devices 5 attached to the neck 6 of the corresponding animal 2 by the corresponding strap 21 as already described. Initially, as the devices 5 are being attached to the animals 2, the identifying codes of the respective devices 5 are sequentially read from the memory chips 40 of the devices 5 by the smart phone 44 which is programmed with the appropriate app. The identifying codes of the devices 5 are read out from the memory chips 31 by the smart phone 44 through the NFC modules 43 of the respective devices 5 in NFC protocol. The identifying codes of the respective devices 5 are stored and cross-referenced in the smart phone 44 with identifying codes of the corresponding animals 2. The identifying codes of the animals may be codes assigned to the animals by the farmer, or alternatively, may be national identifying codes issues by the State which identify the respective animals. The cross-referenced identifying codes of the devices 5 and the corresponding animals 2 are uploaded to the cloud computer server 10 by the smart phone 44 and stored also in the cloud computer server 10 so that the cloud computer server 10 can readily identify the animals from the corresponding identifying codes of the respective devices 5.

If any programming or reprogramming of the microprocessors 30 in the respective devices 5 is required, the necessary programming and reprogramming is carried out by the smart phone 44 operating under the control of the app through the NFC modules 43 of the respective devices 5.

The microprocessor 30 of each device 5 continuously samples the first and second signals from the accelerometer 28 as already described, and at the end of each first predefined time period determines the state of the animal for that first predefined time period, be it ruminating, resting, feeding, or be it in one of the three activity states. The number of times the animal is in the respective states during each second predefined time period is stored in the memory chip 31 cross-referenced with the corresponding states for subsequent transmission by the device 5. As the animal 2 visits the locations at which transmitters 45 are located, and a signal identifying the location is received by the receiver 42 of the corresponding device 5, the identity of the location is read by the microprocessor 30, and is stored in the memory chip 31, together with the time of the visit to the location and the duration of the visit to the location. It will be appreciated that the data relating to the states of the animal and the locations visited by the animal may be stored in memory of the microprocessor 30 or in a separate memory chip to the memory chip 40, instead of the memory chip 40.

As each animal 2 comes within range of the transceiver 14 of the relay station 12, the device 5 of that animal is activated in response to the wake-up signal transmitted by the transceiver 14 of the relay station 12, and the device 5 transmits through the transceiver 41 operating in the low powered mode the data relating to the states of the animal 2 during the second predefined time periods since the last transmission from that device 5 was made, as well as the data relating to the locations visited by the animal 2 since the last transmission from that device was made. The data relating to the state of the animal 2 and the locations visited by the animal 2 received by the transceiver 14 of the relay station 12 is then relayed through the GSM module 15 of the relay station 12 to the cloud computer server 10. The cloud computer server 10 then carries out further analysis of the received data to determine the state of the health of the animal 2 from the received data and other issues relating to the animal.

If the microprocessor 30 of any of the devices 5 determines that the corresponding animal 2 remains in a highly active state during a predefined number of consecutive second predefined time periods which could be indicative of oestrus, the transceiver 41 is operated in the high power mode, and the alert signal is transmitted for reception by the relay station 12, which is then relayed to the cloud computer server 10 by the relay station 12. The alert signal includes the identifying code of the device 5 and data relating to the highly active state of the animal 2 over the relevant predefined number of second predefined time periods.

If the microprocessor 30 of any of the devices 5 determines that the corresponding animal remains in a resting state continuously for a predefined number of consecutive second predefined time periods, which could be indicative of an injured, lame or ill animal, the microprocessor 30 operates the transceiver 41 in the high power mode to transmit the alert signal, which in this case includes the identifying code of the device 5 and data relating to the resting state of the animal over the relevant predefined number of second predefined time periods for reception by the relay station 12. The relay station 12 then relays the alert signal to the cloud computer server 10.

On receipt of the alert signal or signals from corresponding ones of the device 5, the cloud computer server analyses the alert signals, and the data contained therein, and determines whether an emergency state exists in the relevant animal 5. If so, the cloud computer server 10 alerts the farmer by any suitable communication means, for example, by an SMS message transmitted to the smart phone 44 or a mobile phone of the farmer over a telecommunications network, or by a voice message transmitted to a mobile phone or a landline phone of the farmer.

If on analysing the data periodically received from any of the devices 5 relating to the states of the corresponding animals, and the locations visited by the corresponding animals, the cloud computer server detects any issues relating to any of the animals 2 which should be brought to the attention of the farmer, an appropriate message is transmitted by the cloud computer 10 by any suitable means for reception by the farmer, which may be an SMS message or a voice message transmitted by a telecommunications network to the smart phone 44, a mobile phone or a landline phone of the farmer.

Additionally, or alternatively, messages from the cloud computer server 10 to be communicated to the farmer may be communicated via the internet to the smart mobile phone 44 of the farmer, or to a computer of the farmer, for example, a desktop computer, a laptop computer, a tablet computer or indeed any other suitable computer device.

The cloud computer server 10 is also configured to permit downloading of data by a farmer to the smart phone 44 of the farmer, and/or to a computer of the farmer, such as a desktop computer, a laptop computer, a tablet computer or the like. Such data which would be downloadable from the cloud computer server 10 to the farmer would be similar to that uploaded to the cloud computer server by the relay station 12, as well as data relating to and/or resulting from analysis carried out by the cloud computer server 10 on the data received from the devices 5.

All data stored in the devices 5 is downloadable directly onto the smart phone 44 or indeed any smart device, for example, a tablet computer or the like by NFC protocol. To download data stored in any one of the devices 5 to the smart phone 44 or any other such smart device, the smart phone 44 or smart device operating under the control of the app is brought into close proximity within 50 mm of the device 5 from which the data is to be downloaded. An activation signal is produced by the smart phone 44 and is transmitted in an NFC protocol for reception by the NFC module 43 of the device 5. On receipt of the activation signal, the microprocessor 30 is operated to download the data in an NFC protocol through the NFC module 43 to the smart phone 44 or smart device. The data relating to the states of the animal and the locations visited by the animal which is stored in the memory chip 31 is packaged in data packets which include the identity code of the device 5 and the data relating to the states of the animal and the locations visited by the animal 2 as already described prior to downloading to the smart phone 44 or smart device.

Other data relating to the animals may be uploaded to the devices 5 of the corresponding animals 2 by the smart phone 44, and this data may also be uploadable to the cloud computer server 10.

While the signals indicative of the acceleration to which the accelerometer is subjected along the X and Y axes only have been used in detecting the states of the animal, it is envisaged that the signals indicative of the acceleration to which the accelerometer is subjected along the three axes at right angles to each other, namely, the X, Y and Z axes, may be used in detecting the states of the animal. It is envisaged that an animal lying on its side could be detected from signals indicative of the acceleration to which the accelerometer is subjected along the Z-axis. It is also envisaged that a more accurate indication of the activity of the animal could be determined by using the signals from the accelerometer indicative of the acceleration to which the accelerometer is subjected along both the X and the Z axes. In particular, it is possible that by using the signals indicative of the acceleration to which the accelerometer is subjected along the X and Z axes, it may be possible to differentiate between motive movement of the animal, and other movement of the animal, such as movement of the head and neck of the animal relative to the trunk of the animal.

It is also envisaged that by reading signals from the accelerometer indicative of the acceleration to which the accelerometer is subjected along the Z-axis, if the devices are secured to the animal with the Z-axis appropriately located and extending substantially horizontally and transversely relative to the neck of the animal, the signals read from the accelerometer indicative of the acceleration to which the accelerometer is subjected along the Z-axis would be indicative of an animal lying on its side if the animal were lying on its side. This data could also be subsequently analysed by the cloud computer server, and if the animal were detected to be lying on its side for extended periods, this could be an indication of an injury or ill health of the animal.

While the devices 5 have been described as comprising an acceleration sensor provided by a three axis accelerometer, any other suitable acceleration sensor could be provided, for example, a single axis accelerometer would be sufficient for producing the first signal indicative of movement of the head of the animal, or a two axis accelerometer would be sufficient for producing both the first and second signals. Alternatively, a single axis accelerometer may be provided for producing the first signal, and any suitable sensor may be provided for producing the second signal which is indicative of the raised or lowered state of the head of the animal, for example, it is envisaged that a tilt switch could be provided for producing a signal indicative of the state of the head of the animal.

Additionally, it will be appreciated that while the devices according to the invention have been described as comprising a microprocessor for processing the signals read from the accelerometer, in certain cases, it is envisaged that the microprocessor may be dispensed with, and the processing of the signals produced by the accelerometer would be carried out remotely, for example, in the cloud computer, a mobile smart phone or the like, or in a computer in the relay station or in a base station computer. In which case, it is envisaged that the raw data produced by the accelerometer would be transmitted unprocessed by the devices to the relay station, the cloud computer server, mobile smart phone or other such remote device.

Additionally, the microprocessor 30 in the devices could be of sufficient capacity, and could be programmed to carry out further analysis on board on the devices whereby the states of the animals during the second predefined time periods, and the locations visited by the animal during the second predefined time periods would be further analysed in order to determine the health, and other issues relating to the relevant animal. In which case, the further processed data would be transmitted to the relay station 12 and in turn relayed to the cloud computer server. Alternatively, the devices may be configured to communicate with a remote computer, for example, a desktop computer, a laptop computer, a tablet computer, or a smart mobile phone of the farmer to provide the farmer with the analysis of the relevant data, and to alert the farmer to any emergencies.

It will also be appreciated that while the devices have been described as being secured to the side of the neck of the animal by a strap, the devices may be secured in any suitable position on the neck of the animal. Indeed, it is envisaged that the devices may be secured to the head or on any other suitable part of the animal.

It will also be appreciated that while the system has been described as comprising a single relay station, in certain cases, a plurality of the relay stations may be provided spaced apart at suitable locations in a field or fields. Alternatively, the relay station may be omitted, and each device would be provided with a GSM module or other suitable communicating means to communicate with the cloud computer server.

While it is desirable, it is not essential that the devices should comprise an NFC module, and the receiver 42 could also be dispensed with if a record of predefined locations visited by the animal is not required.

It will be appreciated that while the devices, the method and the system according to the invention have been described for detecting a number of specific states of a cow, the devices, method and system may be provided for detecting only one or some of the specific states described. Indeed, it is also envisaged that the devices, the method and system according to the invention may be provided for detecting additional other states of a cow or other animal. Needless to say, it will be appreciated that the device, the method and the system according to the invention may be used for detecting states of any other animals besides cows.

It is also envisaged that the devices may be secured to the animals by other means besides a strap, for example, in certain cases, it is envisaged that the devices may be implanted in the animals at appropriate locations, and when implanted could be located relatively closely to the skin of the animal in order to facilitate Near Field Communications with the devices.

While the devices 5 have been described as receiving transmitted identification signals of the respective predefined locations on visiting of such predefined locations by an animal, it is envisaged that instead of transmitters for transmitting identification signals being provided at each predefined location, an RFID device may be provided at each predefined location, which on transmission of a signal by the transceiver 41 of the devices 5 would reflect and alter the transmitted signal so that the reflected signal would include the identification of the corresponding predefined location.

Additionally, it is envisaged that in order to save power, the devices 5 may be operated to minimise the number of transmissions of data from the devices 5 to the relay station. This would be carried out by preventing transmissions to the relay station unless a predefined time period had elapsed since the last transmission had been made by the device 5.

While the relay station has been described as communicating with a cloud computer server through a GSM module, any other suitable communicating means for communicating between the relay station and the cloud computer may be provided. Indeed, it is also envisaged that instead of or as well as communicating with a cloud computer server, the relay station, or indeed the devices themselves may be configured to communicate directly with a computer of the farmer, for example, with a desktop computer, a laptop computer, a tablet computer or the like which could be housed in the house of the farmer or the office of the farmer. In which case, the computer of the farmer would be appropriately programmed and configured to produce similar data to that produced by the cloud computer server, and the computer of the farmer would also be configured to communicate directly with the smart phone or other smart mobile device for uploading data to the computer of the farmer, or for downloading data from the computer of the farmer.

It is also envisaged that instead of the Near Field Communications Module, other suitable communication modules which are capable of communicating with a mobile smart device within a relatively short range could be provided in the devices. Such a communication module which would be suitable for communicating with a smart phone or other smart phone mobile device would be a Bluetooth low energy communication module.

While the routine described with reference to FIGS. 5a to 5e has been described with the steps of the routine being carried out in a particular order, it will be readily apparent to those skilled in the art that the steps of the routine may be carried out in any other suitable or desired order without departing from the scope of the invention.

The invention claimed is:

1. A method for detecting at least one detectable state of an animal, the method comprising:
   locating an acceleration sensor on or in the animal, the acceleration sensor configured to produce signals indicative of movement of the head of the animal,
   providing a signal processor configured to read signals from the acceleration sensor,
   operating the signal processor
      to read a first signal from the acceleration sensor indicative of movement of the head of the animal,
      to compute a mean magnitude value of the first signal during each predefined time period of a plurality of predefined time periods,
      to count the positive and negative peaks of the first signal during each predefined time period, absolute magnitude values of which with reference to a mean magnitude value lie within a predefined range of absolute magnitude values, and
      to compute a maximum peak to peak value of the first signal during each predefined time period as a sum of absolute magnitude values of a maximum positive peak value with reference to the mean magnitude value and a maximum negative peak value with reference to the mean magnitude value of the first signal during that predefined time period,
   wherein the signal processor is configured to detect the detectable state of the animal as ruminating in any one of the predefined time periods in response to at least one of
      the count of the positive and negative peaks of the first signal which lie within the predefined range of absolute magnitude values exceeding a predefined ruminating threshold count during that predefined time period, and
      the computed maximum peak to peak value of the first signal lying between a lower predefined peak to peak threshold value and an upper predefined peak to peak threshold value during that predefined time period.

2. A method as claimed in claim 1 in which the signal processor is configured to detect ruminating in any one of the predefined time periods in response to the count of the positive and negative peaks of the first signal which lie within the predefined range of absolute magnitude values exceeding a predefined ruminating threshold count during that predefined time period, and the computed maximum peak to peak value of the first signal lying between the lower predefined peak to peak threshold value and the upper predefined peak to peak threshold value during that predefined time period.

3. A method as claimed in claim 1 in which the signal processor is configured to detect one of the detectable states of the animal as resting in any one of the predefined time periods in response to at least one of the count of the positive and negative peaks of the first signal which lie within the predefined range of absolute magnitude values not exceeding the ruminating predefined threshold count during that predefined time period, and the computed maximum peak to peak value of the first signal not exceeding a resting predefined peak to peak threshold value during that predefined time period.

4. A method as claimed in claim 3 in which the signal processor is configured to detect one of the detectable states of the animal as a feeding state in any one of the predefined time periods in response to at least one of the maximum peak to peak value of the first signal being greater than or equal to the resting predefined peak to peak threshold value during that predefined time period, and either one of the following:

the count of the positive and negative peaks of the first signal, the absolute magnitude values of which lie within the predefined range of absolute magnitude values exceeding a predefined feeding threshold count during that predefined time period, and a second signal from a head status sensor attached to the animal indicative of raised and lowered states of the head of the animal being indicative of the head of the animal being in the lowered state during that predefined time period.

5. A method as claimed in claim 4 in which the signal processor is configured to detect one of the detectable states of the animal as an active state in response to the animal being detected as not being ruminating, resting or feeding in any one of the predefined time periods.

6. A method as claimed in claim 4 in which the acceleration sensor comprises an accelerometer configured to produce the first signal indicative of acceleration to which the accelerometer is subjected along a first axis thereof, and the second signal indicative of acceleration to which the accelerometer is subjected along a second axis thereof perpendicular to the first axis, and the accelerometer is attached to the animal with the first axis thereof extending substantially perpendicularly to the back of the neck of the animal, and in a generally upwardly, downwardly direction, and the second axis thereof extending substantially parallel to the back of the neck of the animal.

7. A method as claimed in claim 1 in which the signal processor is configured to detect the detectable state of the animal as a high activity state in any one of the predefined time periods in response to the count of the positive and negative peaks of the first signal, the absolute magnitude values of which with reference to the mean magnitude value of the first signal exceed a first predefined peak threshold value during that predefined time period exceeding a first predefined peak threshold count during that predefined time period.

8. A method as claimed in claim 7 in which the signal processor is configured to detect one of the detectable states of the animal as a medium activity state in any one of the predefined time periods in response to one of the count of the positive and negative peaks of the first signal, the absolute magnitude values of which with reference to the mean magnitude value of the first signal exceed the first predefined peak threshold value lying between a second predefined peak threshold count and one less than the first predefined peak threshold count during that predefined time period, and the count of the positive and negative peaks of the first signal, the absolute magnitude values of which with reference to the mean magnitude value of the first signal exceed a second predefined peak threshold value during that predefined time period exceeding a third predefined peak threshold count during that predefined time period.

9. A method as claimed in claim 8 in which the signal processor is configured to detect one of the detectable states of the animal as a low activity state in any one of the predefined time periods in response to the computed maximum peak to peak value of the first signal exceeding a resting predefined peak to peak threshold value during that predefined time period, and the count of the positive and negative peaks, the absolute magnitude values of which with reference to the mean magnitude value of the first signal exceed the second predefined peak threshold value during that predefined time period being less than the third predefined peak threshold count during that predefined time period.

10. A method as claimed in claim 1 in which the number of the predefined time periods the animal is detected as being in each detectable state is stored.

11. A method as claimed in claim 1 in which the number of the predefined time periods the animal is detected as being in each detectable state is stored and analysed by a computing means.

12. A method as claimed in claim 11 in which the computing means is a remotely located computing means, and the stored data relating to the number of the predefined time periods the animal is in each detectable state is wirelessly communicated to the remotely located computing means.

13. A method as claimed in claim 12 in which the stored data relating to the number of the predefined time periods the animal is in each detectable state is wirelessly communicated to the remotely located computing means by a relay station.

14. A method as claimed in claim 1 in which the method further comprises the step of, when said detectable state of the animal is detected as ruminating, providing an indication of the detected ruminating state at a location remote from said animal.

15. A method as claimed in claim 1 in which data indicative of at least one predefined location visited by the animal is stored, and one of the time at which the animal visited the at least one predefined location and the duration of the visit to the at least one predefined location is stored.

16. A device for detecting at least one detectable state of an animal, the device being configured for locating on or in the animal and comprising:

an acceleration sensor configured to produce signals indicative of movement of a head of the animal, and a signal processor configured to read a first signal from the acceleration sensor indicative of movement of the head of the animal, compute a mean magnitude value of the first signal during each predefined time period of a plurality of predefined time periods, count positive and negative peaks of the first signal during each predefined time period, absolute magnitude values of which with reference to the mean magnitude value lie within a predefined range of absolute magnitude values, and compute the maximum peak to peak value of the first signal during each predefined time period as a sum of the absolute magnitude values of a maximum positive peak value with reference to the mean magnitude value and a maximum negative peak value with reference to the mean magnitude value of the first signal during that predefined time period wherein the signal processor is configured to detect the detectable state of the animal as ruminating in any one of the predefined time periods in response to at least one of the count of the positive and negative peaks of the first signal which lie within the predefined range of absolute magnitude values exceeding a predefined ruminating threshold count during that predefined time period, and the computed maximum peak to peak value of the first signal lying between a lower predefined peak to peak threshold value and an upper predefined peak to peak threshold value during that predefined time period.

17. A device as claimed in claim 16 in which the signal processor is configured to detect ruminating in any one of the predefined time periods in response to the count of the positive and negative peaks of the first signal which lie within the predefined range of absolute magnitude values exceeding a predefined ruminating threshold count during that predefined time period, and the computed maximum peak to peak value of the first signal lying between the lower predefined peak to peak threshold value and the upper predefined peak to peak threshold value during that predefined time period.

18. A device as claimed in claim 16 in which the signal processor is configured to detect one of the detectable states of the animal as resting in any one of the predefined time periods in response to at least one of the count of the positive and negative peaks of the first signal which lie within the predefined range of absolute magnitude values not exceeding the ruminating predefined threshold count during that predefined time period, and the computed maximum peak to peak value of the first signal not exceeding a resting predefined peak to peak threshold value during that predefined time period.

19. A device as claimed in claim 18 in which the signal processor is configured to detect one of the detectable states of the animal as a feeding state in any one of the predefined time periods in response to at least one of the maximum peak to peak value of the first signal being greater than or equal to the resting predefined peak to peak threshold value during that predefined time period, and either one of the following:

the count of the positive and negative peaks of the first signal, the absolute magnitude values of which lie within the predefined range of absolute magnitude values exceeding a predefined feeding threshold count during that predefined time period, and a second signal from a head status sensor attached to the animal indicative of raised and lowered states of the head of the animal being indicative of the head of the animal being in the lowered state during that predefined time period.

20. A device as claimed in claim 19 in which the acceleration sensor comprises the head status sensor, and the acceleration sensor is configured to produce the second signal indicative of the raised and lowered states of the head of the animal.

21. A device as claimed in claim 19 in which the signal processor is configured to detect one of the detectable states of the animal as an active state in response to the animal being detected as not being ruminating, resting or feeding in any one of the predefined time periods.

22. A device as claimed in claim 16 in which the device further comprises a state notification means for, when said detectable state of the animal is detected as ruminating, providing an indication of the detected ruminating state at a location remote from said animal.

23. A device as claimed in claim 16 in which the device comprises a near field communications (NFC) module for facilitating communicating in an NFC protocol between the device and a powered mobile smart device.

24. A system for determining at least one detectable state of an animal, the system comprising the device as claimed in claim 16, and a remote computing means configured to wirelessly receive data from the device indicative of the state of the animal.

25. A device as claimed in claim 16 in which the signal processor is configured to detect the detectable state of the animal as a high activity state in any one of the predefined time periods in response to the count of the positive and negative peaks of the first signal, the absolute magnitude values of which with reference to the mean magnitude value of the first signal exceed a first predefined peak threshold value during that predefined time period exceeding a first predefined peak threshold count during that predefined time period.

26. A device as claimed in claim 25 in which the signal processor is configured to detect one of the detectable states of the animal as a medium activity state in any one of the predefined time periods in response to one of the count of the positive and negative peaks of the first signal, the absolute magnitude values of which with reference to the mean magnitude value of the first signal exceed the first predefined peak threshold value lying between a second predefined peak threshold count and one less than the first predefined peak threshold count during that predefined time period, and the count of the positive and negative peaks of the first signal, the absolute magnitude values of which with reference to the mean magnitude value of the first signal exceed a second predefined peak threshold value during that predefined time period exceeding a third predefined peak threshold count during that predefined time period.

27. A device as claimed in claim 26 in which the signal processor is configured to detect one of the detectable states of the animal as a low activity state in any one of the predefined time periods in response to the computed maximum peak to peak value of the first signal exceeding a resting predefined peak to peak threshold value during that predefined time period, and the count of the positive and negative peaks, the absolute magnitude values of which with reference to the mean magnitude value of the first signal exceed the second predefined peak threshold value during that predefined time period being less than the third predefined peak threshold count during that predefined time period.

* * * * *